US008663201B2

(12) United States Patent
Hill et al.

(10) Patent No.: US 8,663,201 B2
(45) Date of Patent: Mar. 4, 2014

(54) INFUSION DEVICE

(75) Inventors: Michael A. Hill, Santa Monica, CA (US); Ulrich Rankers, Livermore, CA (US); Sheldon B. Moberg, Thousand Oaks, CA (US); Daniel Chan Chiu, Los Angeles, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 0 days.

(21) Appl. No.: 13/237,558

(22) Filed: Sep. 20, 2011

(65) Prior Publication Data

US 2012/0010562 A1 Jan. 12, 2012

Related U.S. Application Data

(60) Division of application No. 12/317,556, filed on Dec. 23, 2008, now abandoned, which is a continuation-in-part of application No. 11/204,667, filed on Aug. 16, 2005, now abandoned.

(51) Int. Cl.
*A61K 9/22* (2006.01)
*A61B 5/00* (2006.01)

(52) U.S. Cl.
USPC .................... 604/890.1; 600/316; 600/365

(58) Field of Classification Search
USPC ......... 604/65, 246–256, 890.1; 600/316, 347, 600/365
See application file for complete search history.

(56) References Cited

U.S. PATENT DOCUMENTS

| | | | |
|---|---|---|---|
| 4,433,072 A | 2/1984 | Pusineri et al. | |
| 4,494,950 A | 1/1985 | Fischell | |
| 4,562,751 A | 1/1986 | Nason et al. | |
| 4,601,707 A | 7/1986 | Albisser et al. | |
| 4,671,288 A | 6/1987 | Gough | |

(Continued)

FOREIGN PATENT DOCUMENTS

| | | |
|---|---|---|
| EP | 0695017 A2 | 1/1996 |
| EP | 1 191 660 A2 | 3/2002 |

(Continued)

OTHER PUBLICATIONS

Reach et al., "Experience with an implantable glucose sensor as a prerequisite of an artificial beta cell," Biomed. Biochim. Acta, 1984, pp. 577-584, vol. 5.

(Continued)

*Primary Examiner* — Victoria P Shumate
(74) *Attorney, Agent, or Firm* — Pillsbury Winthrop Shaw Pittman LLP

(57) ABSTRACT

An infusion system that includes a controller device and a communication system to provide for two-way communication between the controller device and an infusion device that controls delivery of fluids to a user's body. Either the controller device or the infusion device may be integrated with a characteristic determining device in a single housing. The housing, in turn, may include a test-strip receptacle and an illuminator disposed so as to illuminate an area covering the receptacle and a test-strip inserted therein. The illuminator may be configured to be activated automatically when a test strip is inserted into the receptacle, selectively by the user via a button, key, or similar mechanism, and/or when the ambient light level, measured, e.g., with a light sensor, falls below a predetermined intensity. The illuminator may be a LED emitting white light, and may provide illumination at various levels of intensity.

21 Claims, 10 Drawing Sheets

(56) References Cited

U.S. PATENT DOCUMENTS

| | | | |
|---|---|---|---|
| 4,678,408 A | 7/1987 | Nason et al. |
| 4,685,903 A | 8/1987 | Cable et al. |
| 4,731,726 A | 3/1988 | Allen, III |
| 4,781,798 A | 11/1988 | Gough |
| 4,871,351 A | 10/1989 | Feingold |
| 4,908,523 A | 3/1990 | Snowden et al. |
| 5,080,653 A | 1/1992 | Voss et al. |
| 5,097,122 A | 3/1992 | Colman et al. |
| 5,101,814 A | 4/1992 | Palti |
| 5,108,819 A | 4/1992 | Heller et al. |
| 5,165,407 A | 11/1992 | Wilson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,320,725 A | 6/1994 | Gregg et al. |
| 5,322,063 A | 6/1994 | Allen et al. |
| 5,356,786 A | 10/1994 | Heller et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,497,772 A | 3/1996 | Schulman et al. |
| 5,543,326 A | 8/1996 | Heller et al. |
| 5,569,186 A | 10/1996 | Lord et al. |
| 5,586,553 A | 12/1996 | Halili et al. |
| 5,593,390 A * | 1/1997 | Castellano et al. ........... 604/187 |
| 5,593,852 A | 1/1997 | Heller et al. |
| 5,660,163 A | 8/1997 | Schulman et al. |
| 5,665,065 A | 9/1997 | Colman et al. |
| 5,665,222 A | 9/1997 | Heller et al. |
| 5,684,384 A | 11/1997 | Barkat et al. |
| 5,717,308 A | 2/1998 | Nishitani et al. |
| 5,728,074 A * | 3/1998 | Castellano et al. ........... 604/207 |
| 5,750,926 A | 5/1998 | Schulman et al. |
| 5,779,665 A | 7/1998 | Mastrototaro et al. |
| 5,791,344 A | 8/1998 | Schulman et al. |
| 5,800,386 A | 9/1998 | Bellifemine |
| 5,814,972 A | 9/1998 | Shimada et al. |
| 5,904,708 A | 5/1999 | Goedeke |
| 5,917,346 A | 6/1999 | Gord et al. |
| 5,925,021 A | 7/1999 | Castellano et al. |
| 5,965,380 A | 10/1999 | Heller et al. |
| 5,972,199 A | 10/1999 | Heller et al. |
| 5,999,848 A | 12/1999 | Gord et al. |
| 5,999,849 A | 12/1999 | Gord et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,169,387 B1 | 1/2001 | Kaib |
| 6,175,752 B1 | 1/2001 | Say et al. |
| 6,192,891 B1 * | 2/2001 | Gravel et al. ............... 604/187 |
| 6,259,937 B1 | 7/2001 | Schulman et al. |
| 6,329,161 B1 | 12/2001 | Heller et al. |
| 6,472,122 B1 | 10/2002 | Schulman et al. |
| 6,475,750 B1 | 11/2002 | Han et al. |
| 6,478,440 B1 | 11/2002 | Jaworski et al. |
| 6,484,046 B1 | 11/2002 | Say et al. |
| 6,503,381 B1 | 1/2003 | Gotoh et al. |
| 6,514,718 B2 | 2/2003 | Heller et al. |
| 6,540,672 B1 * | 4/2003 | Simonsen et al. ........... 600/300 |
| 6,554,798 B1 | 4/2003 | Mann et al. |
| 6,558,320 B1 | 5/2003 | Causey, III et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,565,509 B1 | 5/2003 | Plante et al. |
| 6,570,503 B1 | 5/2003 | Ulert et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,733,471 B1 | 5/2004 | Ericson et al. |
| 6,746,582 B2 | 6/2004 | Heller et al. |
| 6,749,740 B2 | 6/2004 | Liamos et al. |
| 6,752,787 B1 | 6/2004 | Causey et al. |
| 6,781,921 B2 | 8/2004 | Markart |
| 6,809,653 B1 | 10/2004 | Mann et al. |
| 6,875,195 B2 * | 4/2005 | Choi ........................ 604/66 |
| 6,881,551 B2 | 4/2005 | Heller et al. |
| 6,893,545 B2 | 5/2005 | Gotoh et al. |
| 6,916,159 B2 | 7/2005 | Rush et al. |
| 6,932,894 B2 | 8/2005 | Mao et al. |
| 6,936,029 B2 | 8/2005 | Mann et al. |
| 6,942,518 B2 | 9/2005 | Liamos et al. |
| 6,945,934 B2 | 9/2005 | Bardy |
| 7,278,983 B2 | 10/2007 | Ireland et al. |
| 7,727,148 B2 | 6/2010 | Talbot et al. |
| 2002/0036479 A1 | 3/2002 | Aoyagi et al. |
| 2002/0045808 A1 | 4/2002 | Ford et al. |
| 2002/0058906 A1 | 5/2002 | Lebel et al. |
| 2002/0065454 A1 | 5/2002 | Lebel et al. |
| 2002/0082665 A1 | 6/2002 | Haller et al. |
| 2002/0107476 A1 | 8/2002 | Mann et al. |
| 2002/0151771 A1 | 10/2002 | Braun et al. |
| 2002/0161288 A1 | 10/2002 | Shin et al. |
| 2002/0169636 A1 | 11/2002 | Eggers et al. |
| 2002/0198513 A1 | 12/2002 | Lebel et al. |
| 2003/0060765 A1 | 3/2003 | Campbell et al. |
| 2003/0065308 A1 | 4/2003 | Lebel et al. |
| 2003/0078560 A1 | 4/2003 | Miller et al. |
| 2003/0088166 A1 | 5/2003 | Say et al. |
| 2003/0140929 A1 | 7/2003 | Wilkes et al. |
| 2003/0152823 A1 | 8/2003 | Heller et al. |
| 2003/0168338 A1 | 9/2003 | Gao et al. |
| 2003/0176183 A1 | 9/2003 | Drucker et al. |
| 2003/0181851 A1 | 9/2003 | Mann et al. |
| 2003/0181852 A1 | 9/2003 | Mann et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0212317 A1 | 11/2003 | Kovatchev et al. |
| 2003/0212379 A1 | 11/2003 | Bylund et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey et al. |
| 2004/0074785 A1 | 4/2004 | Holker et al. |
| 2004/0093167 A1 | 5/2004 | Braig et al. |
| 2004/0111017 A1 | 6/2004 | Say et al. |
| 2004/0122353 A1 | 6/2004 | Shahmirian et al. |
| 2004/0167464 A1 | 8/2004 | Ireland et al. |
| 2004/0193025 A1 | 9/2004 | Steil et al. |
| 2004/0199409 A1 | 10/2004 | Brown |
| 2004/0215492 A1 | 10/2004 | Choi |
| 2004/0254434 A1 | 12/2004 | Goodnow et al. |
| 2005/0038332 A1 | 2/2005 | Saidara et al. |
| 2005/0058181 A1 | 3/2005 | Lyle et al. |

(56) References Cited

U.S. PATENT DOCUMENTS

| | | |
|---|---|---|
| 2005/0059895 A1 | 3/2005 | Brown |
| 2005/0065464 A1 | 3/2005 | Talbot et al. |
| 2005/0137530 A1 | 6/2005 | Campbell et al. |
| 2005/0137573 A1 | 6/2005 | McLaughlin |
| 2005/0143635 A1 | 6/2005 | Kamath et al. |
| 2005/0154271 A1 | 7/2005 | Rasdal et al. |
| 2005/0182308 A1 | 8/2005 | Bardy |
| 2005/0197553 A1 | 9/2005 | Cooper |
| 2005/0214585 A1 | 9/2005 | Li et al. |
| 2005/0239156 A1 | 10/2005 | Drucker et al. |
| 2005/0273080 A1 | 12/2005 | Paul |
| 2006/0025663 A1 | 2/2006 | Talbot et al. |
| 2006/0058627 A1 | 3/2006 | Flaherty et al. |
| 2006/0128324 A1 | 6/2006 | Tan et al. |
| 2006/0173260 A1 | 8/2006 | Gaoni et al. |
| 2006/0182658 A1 | 8/2006 | Wu et al. |
| 2006/0221594 A1 | 10/2006 | Thuot Rann et al. |
| 2006/0259676 A1 | 11/2006 | Oberding et al. |
| 2006/0261781 A1 | 11/2006 | Oberding et al. |
| 2006/0277411 A1 | 12/2006 | Reynolds et al. |
| 2007/0004969 A1 | 1/2007 | Kong et al. |
| 2007/0093786 A1 | 4/2007 | Goldsmith et al. |
| 2007/0100222 A1 | 5/2007 | Mastrototaro et al. |
| 2007/0106133 A1 | 5/2007 | Satchwell et al. |
| 2007/0171037 A1 | 7/2007 | Schofield et al. |
| 2007/0253187 A1 | 11/2007 | Cohan et al. |
| 2008/0086043 A1 | 4/2008 | Heller et al. |
| 2008/0094345 A1 | 4/2008 | Tseng et al. |
| 2008/0103377 A1 | 5/2008 | Brown |
| 2008/0200897 A1 | 8/2008 | Hoss et al. |
| 2008/0212215 A1 | 9/2008 | Schofield et al. |
| 2008/0294024 A1 | 11/2008 | Cosentino et al. |
| 2009/0034958 A1 | 2/2009 | Dierenbach |
| 2009/0098018 A1 | 4/2009 | Bainczyk et al. |
| 2009/0105570 A1 | 4/2009 | Sloan et al. |
| 2009/0227855 A1 | 9/2009 | Hill et al. |
| 2009/0303477 A1 | 12/2009 | Burd |
| 2010/0311181 A1 | 12/2010 | Abraham et al. |

FOREIGN PATENT DOCUMENTS

| | | |
|---|---|---|
| EP | 1 177 802 A1 | 6/2002 |
| EP | 1338295 A1 | 8/2003 |
| GB | 2 395 373 A | 5/2004 |
| JP | HO 9-019086 | 1/1997 |
| JP | HO 9-294330 | 11/1997 |
| JP | 11-149420 | 2/1999 |
| JP | 2002-101574 | 4/2002 |
| WO | WO 91/04601 | 4/1991 |
| WO | WO 95/28878 | 11/1995 |
| WO | WO 96/37246 A1 | 11/1996 |
| WO | WO 97/00708 | 1/1997 |
| WO | WO 00/47109 A1 | 8/2000 |
| WO | WO 00/74752 A1 | 12/2000 |
| WO | WO 01/08551 A2 | 2/2001 |
| WO | WO 02/058537 A2 | 8/2002 |
| WO | WO 2004/009161 | 1/2004 |
| WO | WO 2006/001929 A1 | 1/2006 |

OTHER PUBLICATIONS

Abel et al., "A Method for Evaluating in vivo the Functional Characteristics of Glucose Sensors," Biosensors, 1986, pp. 211-220, vol. 2.
Boguslavsky et al., "Applications of redox polymers in biosensors," Solid State Ionics, 1993, pp. 189-197, vol. 60.
Geise et al., "Electropolymerized 1,3-diaminobenzene for the construction of a 1-1'-dimethylferrocene mediated glucose biosensor," Analytica Chim. Acta.,1993, pp. 467-473, v18.
Gernet et al., "A planar glucose enzyme electrode," Sensors and Actuators, 1989, pp. 537-540, vol. 17, Elsevier Sequoia, Netherlands.
Gernet et al., "Fabrication and Characterization of a Planar Electrochemical Cell and Its Applications as a Glucose Sensor," Sensors and Actuators, 1989, pp. 49-70, vol. 18.
Gorton et al., "Amperometric glucose senosrs based on immobilized glucose-oxidizing enzymes and chemically modified electrodes," Analytica Chim Acta., 1991, pp. 43-54, v. 249.
Gorton et al., "Amperometric biosensors based on an apparent direct electron transfer between electrodes and immobilized peroxidases," Analyst, 1992, pp. 1235-1241, vol. 117.
Gough et al., "Two-Dimensional Enzyme Electrode Sensor for Glucose," Analytical Chemistry, 1985, pp. 2351-2357, vol. 57.
Gregg et al., "Redox polymer films containing enzymes," J. Phys. Chem., 1991, pp. 5970-5975.
Gregg et al., "Cross-Linked Redox Gels Containing Glucose Oxidase for Amperometric Biosensor Applications," Anal. Chem., 1990, pp. 258-263, vol. 62.
Heller et al., "Electrical Wiring of Redox Enzymes," Accounts of Chemical Research, 1990, pp. 128-134, vol. 23, No. 5.
Johnson et al., "In vivo evaluation of an electroenzymatic glucose sensor implanted in subcutaneous tissue," Biosensors & Bioelectronics, 1992, pp. 709-714, vol. 7.
Jonsson et al., "An Electrochemical Sensor for Hydrogen Peroxide Based on Peroxidase Adsorbed on a Spectrographic Graphite Electrode," electroanalysts, 1989, pp. 465-468, v.1.
Kanapieniene et al., "Miniature glucose biosensor with extended linearity," Sensors and Actuators, 1992, pp. 37-40, vol. B, No. 10.
Kawamori et al., "Perfect Normalization of Excessive Glucagon Responses to Intravenous Arginine in Human Diabetes Mellitus With . . . ," Diabetes, 1980, pp. 762-765, vol. 29.
Kimura et al., "An immobilized Enzyme Membrane Fabrication Method using an Ink Jet Nozzle," Biosensors, 1988, pp. 41-52, vol. 4.
Koudelka et al., "In-vivio Behaviour of Hypodermically Implanted Microfabricated Glucose Sensors," Biosensors & Bioelectronics, 1991, pp. 31-36, vol. 6.
Mastrototaro et al., "An electroenzymatic glucose sensor fabricated on a flexible substrate," Sensors and Actuators, 1991, pp. 139-144, vol. 5.
Mastrototaro et al., "An Electroenzymatic Sensor Capable of 72 Hour Continuous Monitoring of Subcutaneous Glucose," 14th Int'l Diabetes Federation Congress, 1991.
McKean et al., "A Telemetry-Instrumentation System for Chronically Implanted Glucose and Oxygen Sensors," IEEE Transactions on Biomedical Eng., 1988, pp. 526-532, vol. 35, No. 7.
Monroe, "Novel implantable glucose sensors," ACL, 1989, pp. 8-16.
Morff et al., "Microfabrication of Reproducible, Economical, Electroenzymatic Glucose Sensors," Annual Int'l Conf. IEEE Eng. in Med. and Bio. Soc., 1990, pp. 483-484, v.12, n.2.
Nakamato et al., "A Lift-Off Method for Patterning Enzyme-Immobilized Membranes in Multi-Biosensors," Sensors and Actuators, 1988, pp. 165-172, vol. 13.
Nishida et al., "Clinical applications of the wearable artificial endocrine pancreas with the newly designed . . . ," Path. and Treat. of NIDDM . . . , 1994, p. 353-358, No. 1057.
Shichiri et al., "An artificial endocrine pancrease—problems awaiting solutions for long term clinical applications of . . . ," Frontiers Med. Biol. Eng., 1991, pp. 283-292, v.3.
Shichiri et al., "Wearable Artificial Endocrine Pancreas with Needle-Type Glucose Sensor," The Lancet, 1982, pp. 1129-1131, vol. 2 (8308).
Shichiri et al., "Telemetry Glucose Monitoring Device with Needle-Type Glucose Sensor," Diabetes Care, May-Jun. 1986, pp. 298-301, vol. 9, No. 3.
Shichiri et al., "Normalization of the Paradoxic Secretion of Glucagen in Diabetics Who Were Controlled by the Artificial Beta Cell," Diabetes, 1979, pp. 272-275, vol. 28.
Shichiri et al., "Closed-Loop Glycemic Control with a Wearable Artificial Endocrine Pancreas," Diabetes, 1984, pp. 1200-1202, vol. 33.
Shichiri et al., "In Vivo Characteristics of Needle-Type Glucose Sensor," Hormone and Metabolic Research, 1988, pp. 17-20, vol. 20.
Shichiri et al., "A Needle-Type Glucose Sensor," Life Support Systems: The Journal of the European Society for Artificial Organs, 1984, pp. 7-9, vol. 2, supplement 1.
Shichiri et al., "The Wearable Artificial Endocrine Pancreas with a Needle-Type Glucose Sensor," Acta Pediatr, Jpn, 1984, pp. 358-370, vol. 26.

(56) References Cited

OTHER PUBLICATIONS

Shichiri et al., "Glycaemic Control in Pancreatectomized Dogs with a Wearable Artificial Endocrine Pancreas," Diabetologica, 1983, pp. 179-184, vol. 24.
Shichiri et al., "Membrane design for extending the long-life of an implantable glucose sensor," Diab. Nutr. Metab., 1989, pp. 309-313, vol. 2.
Shinkai et al., "Molecular Recognition of Mono- and Di-Saccharides by Phenylboronic Acids in Solvent Extraction and as a Monolayer," J. Chem. Soc., 1991, pp. 1039-1041.
Tamiya et al., "Micro Glucose Sensors Using Electron Mediators Immobilized on a Polypyrrole-Modified Electrode," Sensors and Actuators, 1989, pp. 297-307, v.18.
Tsukagoshi et al., "Specific Complexation with Mono- and Disaccharides That Can Be Detected by Circular Dichroism," J. Org. Chem., 1991, pp. 4089-4091, vol. 56.
Urban et al., "Minaturized multi-enzyme biosensors integrated with pH sensors on flexible polymer carriers . . . ," Biosensors & Bioelectronics, 1992, pp. 733-739, vol. 7.
Urban et al., "Miniaturized thin-film biosensors using covalently immobilized glucose oxidase," Biosensors & Bioelectronics, 1991, pp. 555-562, vol. 6.
Velho et al., "In vivo calibration of a subcutaneous glucose sensor for determination of subcutaneous glucose kinetics," Diab. Nutr. Metab., 1988 pp. 227-233, v.3.
Yokoyama et al., "Integrated Biosensor for Glucose and Galactose," Analytica Chimica Acta., 1989, pp. 137-142, vol. 218.
Nishida et al., "Development of a ferrocene-mediated needle-type glucose sensor . . . ," Medical Process Through Technology, 1995, pp. 91-103, vol. 21.
Koudelka et al., "Planar Amperometric Enzyme-Based Glucose Microelectrode," Sensors and Actuators, 1989, pp. 157-165, vol. 18.
Yamasaki et al., "Direct measurement of whole blood glucose by a needle-type sensor," Clinica Chimica Acta., 1989, pp. 93-98, vol. 93.
Sternberg et al., "Study and Development of Multilayer Needle-type Enzyme-based Glucose Microsensors," Biosensors, 1988, pp. 27-40, vol. 4.
Shaw et al., "In vitro testing of a simply constructed, highly stable glucose sensor suitable for implantation . . . ," Biosensors & Bioelectronics, 1991, pp. 401-406, vol. 6.
Poitout et al., "A glucose monitoring system for on line estimation in man of blood glucose concentration using a miniaturized . . . ," Diabetologia, 1993, pp. 658-663, vol. 36.
Hashigushi et al., "Development of a Miniaturized Glucose Monitoring System by Combining a Needle-Type Glucose Sensor . . . ," Diabetes Care, 1994, pp. 387-389, v.17, n.5.
Jobst et al., "Thin-Film Microbiosensors for Glucose-Lactate Monitoring," Anal. Chem., 1996, p. 3173-79, vol. 68.
Shults et al., "A Telemetry-Instrumentation System for Monitoring Multiple Subcutaneously Implanted Glucose Sensors," IEEE Trans. on Biomed. Eng., 1994, pp. 937-942, v41, n.10.
Wang et al., "Needle-Type Dual Microsensor for the Simultaneous Monitoring of Glucose and Insulin," Anal. Chem., 2001, pp. 844-847, vol. 73.
Moussey et al., "Performance of Subcutaneously Implanted Needle-Type Glucose Sensors Employing a Novel Inlayer Coating," Anal. Chem., 1993, 2072-77, vol. 65.
Bindra et al., "Design and In Vitro Studies of a Needle-Type Glucose Sensor for Subcutaneous Monitoring," Anal. Chem., 1991, pp. 1692-1696, vol. 63.
"The World's Smallest PDA Computer Watch", Hammacher Schlemmer Mid Summer 2000 Catalog, p. 3., Mid Summer 2000.
PCT International Search Report, Dec. 12, 2006 (PCT/US2006/031307) (4 pages).
"Battery Bank Switching", Jim T. Wiggenhorn, Motorola Technical Developments, 10, p. 18, Mar. 1990.
PCT International Search Report, May 26, 2008, (PCT/US2007/013249) (7 pages).
PCT International Search Report, Jan. 22, 2008 (PCT/US2007/016199) (5 pages).
PCT International Search Report, Feb. 2, 2007 (PCT/US2006/031310) (3 pages).
International Search Report and Written Opinion of the International Searching Authority, (PCT/US2009/068417) (Apr. 14, 2010) (14 pages).

* cited by examiner

INFUSION DEVICE

RELATED APPLICATION DATA

This is a divisional application of U.S. patent application Ser. No. 12/317,556, filed Dec. 23, 2008, which is a continuation-in-part of U.S. patent application Ser. No. 11/204,667, filed Aug. 16, 2005, which was filed concurrently with U.S. patent application Ser. No. 11/204,583, all of which are herein incorporated by reference.

FIELD OF THE INVENTION

Embodiments of this invention relate generally to infusion systems and methods for delivering fluids into an individual's body. More particularly, embodiments of the invention relate to apparatuses and methods for providing a convenient way in which to monitor and control the fluids delivered to the individual's body, including improved operation of embodiments of the invention in low-light environments.

DESCRIPTION OF RELATED ART

Patients with Type 1 diabetes and some patients with Type 2 diabetes use insulin to control their blood glucose (BG) level. Diabetics must modify their daily lifestyle to keep their body in balance. To do so, diabetics need to keep strict schedules, including ingesting timely nutritious meals, partaking in exercise, monitoring BG levels daily, and adjusting and administering insulin dosages accordingly. Testing of BG levels has been both painful and awkward for the patient. Traditionally, insulin dependent diabetics were required to monitor their BG levels by puncturing a finger tip with a needle. Due to the fact that many patients must conduct such a test multiple times throughout the day to regulate their BG levels, the procedure can be painful and inconvenient.

Typically, patients may employ various calculations to determine the amount of insulin to inject. For example, bolus estimation software is available for calculating an insulin bolus. Patients may use these software programs on an electronic computing device, such as a computer, the Internet, a personal digital assistant (PDA), or an insulin delivery device. Insulin delivery devices include infusion pumps, injection pens, and implantable delivery systems. The better bolus estimation software takes into account the patient's present BG level. Presently, a patient must measure his/her blood glucose using a BG measurement device, such as a test strip meter, a continuous glucose measurement system, or a hospital hemacue. BG measurement devices use various methods to measure the BG level of a patient, such as a sample of the patient's blood, a sensor in contact with a bodily fluid, an optical sensor, an enzymatic sensor, or a fluorescent sensor. In low-light environments, patients may experience difficulty with proper placement of the test strip into the strip port of the BG measurement device.

When the BG measurement device has generated a BG measurement, the measurement is displayed on the BG measurement device. Then the patient may visually read the BG measurement and physically enter the BG measurement into an electronic computing device to calculate a bolus estimate. Finally, once the bolus estimate is calculated, the patient must inject the insulin bolus or program an insulin delivery device to deliver the bolus into their body. Unfortunately, this process is also cumbersome and is subject to transcribing errors—for example, the patient may inaccurately enter the BG measurement that is displayed on the BG measurement device into the electronic computing device. Thus, if the BG measurement is not entered correctly, the bolus estimate is not accurate, which may lead to the delivery of an inappropriate insulin dose. In other devices, the measurement is transmitted to the electronic computing device.

In infusion systems where a display is included for convenient viewing of selected information, such as that requested by the user or an instructed act that was undertaken by the infusion device, the display is generally located on the infusion device. This may be inconvenient for the user to view information because the infusion device is typically secured to or near an infusion site on the user's body. Thus, viewing may require the user to move or manipulate the infusion device to view the display which may lead to improper reading of the display.

BRIEF SUMMARY OF THE INVENTION

In accordance with embodiments of the invention, an infusion system is provided that allows for the control of the delivery of a fluid or medication. An embodiment of the present invention includes a controller device and a therapy/diagnostic device, such as an infusion device. The controller device may be a hand-held device, separate from the infusion device, that allows the user to communicate with the infusion device without actually handling the infusion device.

The controller device includes a housing adapted to be carried by the user and a communication system contained in the housing for transmitting a communication or command from the user to the infusion device. In alternative embodiments, the controller device may receive communications sent from the infusion device or other components of the infusion system, such as for example, a characteristic determining device. Further, the controller device may include a user input device on the controller device housing, such as keys, buttons, or the like, for the user to input data or commands. In addition, or alternatively, the user input device may comprise a touch screen (such as, e.g., one or more of a resistive, capacitive, surface acoustic wave, near field imaging, infrared, and/or other types of touch screen).

The controller device includes on the housing a display that may mimic the display on the infusion device. In certain embodiments, whatever is shown on the infusion device corresponds to that shown and reflected on the display of the controller device. The controller device display shows information according to communications sent to it from the infusion device. The user may more conveniently view what is being processed or acted upon in the infusion device without removing or adjusting the infusion device to view the display. In further embodiments, the controller device may be configured so that the input devices included allow all, or substantially all, viewing and data entry to be performed on the controller device without moving or referring to the infusion device.

Among other advantages, embodiments of the present invention may provide convenience and ease of use. For example, an embodiment with a user interface and display on the controller device may cater to the active lifestyles of many insulin dependent diabetics. A large and simple display minimizes the potential for error in reading and interpreting test data. A small overall size permits discretion during self-monitoring and makes it easy to carry. In another embodiment, the controller device may be integrated with a characteristic determining device into one housing and feature a large target area for strip insertion to make the monitoring procedure fast and accurate. In some embodiments, the controller device display may include a dedicated backlight to facilitate viewing.

In additional embodiments, the controller device may include an illuminator that is disposed so as to illuminate the above-mentioned target area for strip insertion, including the inserted test strip itself. In yet other embodiments, the characteristic determining device may be integrated with the infusion device, rather than with the controller device, into one housing. In this case, the infusion device features a large target area for strip insertion, as well as an illuminator that is configured to illuminate the target area, including the inserted test strip itself. In embodiments of the invention, the illuminator may be activated upon insertion of the test strip, by operation of a button, key, or other mechanism, and/or by feedback from a light sensor when the sensor determines that the available lighting is below a pre-determined level.

The controller device also reflects the other functions that the particular infusion device may show, including a variety of other displays, for example, when the last bolus was administered, when the last alarm occurred, when the last finger stick was taken, past trends, all alarms that occurred in a time period, calibrations, meals, exercise, bolus schedules, temporary basal delivery, diagnostic information, and the like. Whenever a bolus is being delivered, the infusion device can send a message every time a tenth of a unit, or some specified amount, is delivered, which the user may monitor via the controller device display.

In certain embodiments, the infusion device is the central hub with peripheral devices being the controller device and a characteristic determining device. The characteristic determining device is adapted to sense and determine the concentration of an analyte of a patient and directs the infusion device fluid delivery according to the measurements. While the term "analyte" is used herein, it is possible to determine and use other characteristics as well using the same type of system. The control is maintained in the central hub and the infusion device sends out most of the commands. The infusion device also sends requests to receive specific data from the controller device and the characteristic determining device, if one is included.

In particular embodiments, where the controller device is integrated with the characteristic determining device into one housing, the controller device may automatically transmit communications including the data indicative of the determined concentration of the analyte in the user to the infusion device. In other particular embodiments, the controller device further includes a user input device for inputting commands, and transmits the communications to the infusion device in response to a command from the user input device. In additional embodiments, the controller device further includes an indicator to indicate a status of the communication including the data indicative of the determined concentration of the analyte in the user being transmitted from the determining device communication system to the infusion device communication system. Data compression may be employed to speed up communications.

In further embodiments, the infusion device may contain all or substantially all of the intelligence. The amount of time that the controller communicates with the infusion device or other components may be limited to save power in the controller device. For example, radio-frequency (RF) communications may be minimized, such that the marriage between the infusion device and controller occurs once until further communication is necessary to exchange data. The information regarding the screens displayed is sent to the controller, and when the infusion device needs to display a screen, it sends a screen number to the controller. In the case of screen displays, if the data being sent is fixed, then the screen can be simply displayed. If the data is variable, then the variable data is sent with the screen to the infusion device. Exchange IDs, strings to be displayed, and foreign languages are among data that may be sent from the controller. Further commands that may be sent from the infusion device include, among other commands, a command to show a specific screen on the controller device, a command for displaying requested information on the screen, a command for showing the rules for the input devices, a command for showing the intelligence about that screen type (e.g., menus, data entries, etc.), and the like.

The controller device and the infusion device may communicate to one another through wireless or non-wireless methods. Some examples of wireless methods include, by no way in limitation, RF, infrared (IR), 802.15 protocols (e.g., ZIGBEE), 802.11 WiFi, spread spectrum communication (e.g., BLUETOOTH), and frequency hopping communication. Further examples include giving the controller device cellular telephone or pager capabilities. In the alternative, the communication may be wired, such as in hospital use. In a wired embodiment, there may be a tether physically connecting the infusion device to the controller device. In yet another alternative, the controller device and the infusion device could be both wired and wireless—when wired, the two components communicate by wire, and when disconnected, the two components could operate through wireless communication.

In another wireless example, if the user has access to a computer network or phone connection, the user can open communication via the internet to obtain communications from, and send communications to, a nurse, parent, or anyone so desired. A transceiver may be used to facilitate data transfer between the PC and the infusion device. Such a communication may also be used by a party, other than the user, to control, suspend, and/or clear alarms. This embodiment could be very useful for a parent to monitor the infusion system of a child, or for a physician to monitor the infusion system of a patient. As a non-limiting example, further description of a communication station may be found in U.S. Pat. No. 5,376,070, which is herein incorporated by reference. The transceiver may allow patients at home or clinicians in a hospital setting to communicate with the various components of the infusion system via RF telemetry. The transceiver may be used to download device information from the infusion device and sent to the PC when the transceiver is connected in to the serial port of the PC. In embodiments, the transceiver may derive its power from the PC when the two are connected. In this way, the transceiver conveniently does not require a separate power source. In another embodiment, a cellular phone may be used as a conduit for remote monitoring and programming. In yet other embodiments, the controller device may also act as a transceiver, which would eliminate an extra component.

In yet further embodiments, the infusion system includes an infusion device and/or a sensing device. The sensing device includes a sensor and a transmitter in communication with the infusion device. The transmission may occur via wire or wireless methods. The sensing device includes a sensor and a transmitter in communication with the infusion device. The sensing device may sense an analyte of a bodily fluid of the user and provide continuous monitoring of that analyte. The sensing device may be calibrated using data from the infusion device and/or from a characteristic determining device. As noted, the characteristic determining device may be a stand-alone device, or it may be integrated into a single housing with the controller device or the infusion device. In further embodiments, the sensing device senses additional physiological characteristics. In still further embodiments, the system is set up to automatically call for assistance when analytes reach a certain level. The system may be set up to notify others, for example, through a cellular network. In such a manner, the patient's cellular telephone may be used to connect to emergency services. The call may include a global positioning system (GPS) location. GPS functions may be included separately from cellular telephone type functions.

Communications between the system components may be performed in a variety of manners. In an embodiment using RF options, there could be employed a "spread spectrum" where a large range of RFs can be used to relay the communication. In another embodiment, changing frequencies can be used so as to pick up whatever frequency is present. This is known as frequency hopping, where the frequency changes periodically or so to take advantage of all, or substantially all, frequencies available. Another embodiment is one that uses adaptive frequency selection, or Listen Before Talk (LBT), where the devices select the cleanest available channel from those allotted prior to transmitting. In some cases, frequency hopping allows the system to find frequencies that are not being used by other nearby systems and thus avoid interference. In addition, a system may operate in a manner where each component-to-component communication is on a different frequency, or where the delay for each communication is different. Other types of RF, that are not described, may also be used for communication, such as, translation frequency.

BRIEF DESCRIPTION OF THE DRAWINGS

A detailed description of embodiments of the invention will be made with reference to the accompanying drawings, wherein like numerals designate corresponding parts in the figures.

DETAILED DESCRIPTION OF THE INVENTION

In the following description, reference is made to the accompanying drawings which form a part hereof and which illustrate several embodiments of the present inventions. It is understood that other embodiments may be utilized and structural and operational changes may be made without departing from the scope of the present inventions.

Figures 1, 2:
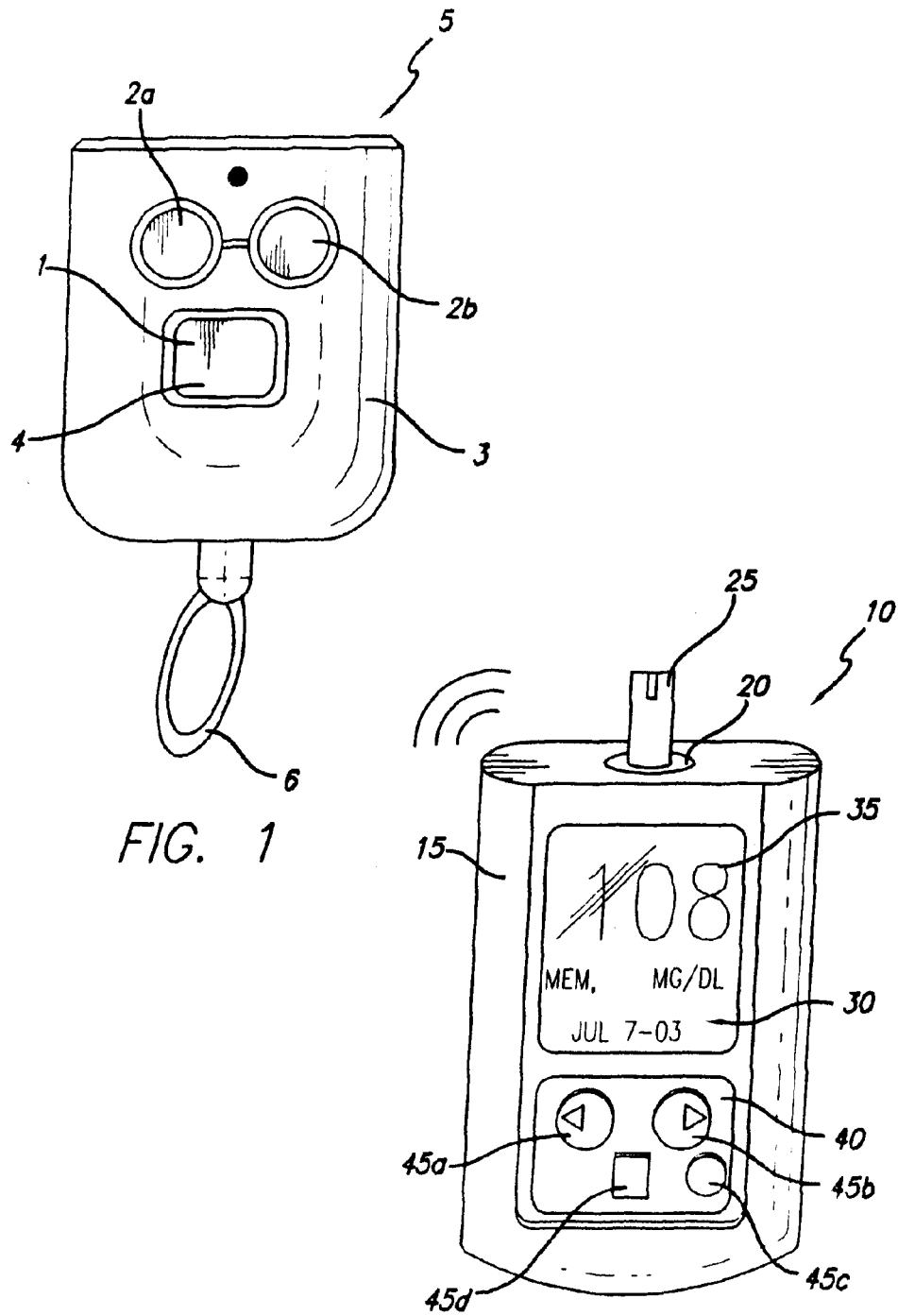
FIG. 1 is a front view of a controller device according to an embodiment of the invention.
FIG. 2 is a front view of a blood glucose meter integrated into a controller device housing according to an embodiment of the invention.

In one embodiment, the controller device is a hand-held device separate from the therapy/diagnostic device, such as an infusion device, that allows the user to communicate with the therapy/diagnostic device without actually handling the device. Other examples of therapy/diagnostic devices include electronic therapy devices and devices that receive diagnostic information from cardiac and other sensors. As illustrated in FIG. 1, the controller device 5 includes a housing 3 adapted to be carried by the user and a communication system (not shown) contained in the housing 3 for transmitting a communication or command from the user to the infusion device. In further embodiments, the controller device 5 may receive communications sent from the infusion device or other components of the infusion system, such as for example, a characteristic determining device. Further, the controller device may include one or more user input devices 2a and 2b on the controller device housing 3, such as keys, buttons, or the like, for the user to input data or commands. The controller device 5 includes a display 4 on the controller device housing 3 which simultaneously displays whatever information and/or graph is being displayed on the infusion device display at that moment. The display 4 allows a user to easily monitor and control what actions are taking place in, or being performed by, the infusion device. In some embodiments, the controller device 5 may further include a backlight 1 in the controller device display 4 for easier viewing. The backlight may be adapted to be in one or more colors, which can be user selectable for personalized use. In further embodiments, the backlight may be adapted to flash and/or turn to a color such as yellow or red when various alerts and alarms take place. In additional embodiments, the controller device 5 may include accessories such as hand straps 6 to provide convenient handling. In particular embodiments, the controller is sized smaller than 6 inches long by 4 inches wide by 1 inch thick.

In certain embodiments, a characteristic determining device that senses and determines the concentration of an analyte of a patient, for example blood glucose ("BG"), and controls the infusion device according to the measurements, may be included in an infusion system with the controller device and the infusion device. The characteristic determining device includes a housing, a receptacle coupled to the housing for receiving and testing an analyte from the user to determine a concentration of the analyte in the user, a processor contained in the housing and coupled to the receptacle for processing the determined concentration of the analyte from the receptacle, and a communication system contained in the housing and coupled to the processor for transmitting a communication including data indicative of the determined concentration of the analyte in the user. In particular embodiments, the characteristic determining device may also include a lancing device coupled to the receptacle for obtaining the analyte from the user.

In embodiments, the infusion device includes a housing adapted to be carried by the user, a drive mechanism contained in the housing and operatively coupled with a reservoir containing the fluid for infusing the fluid into the body of the user, a communication system contained in the housing for receiving the communication including the data indicative of the determined concentration of an analyte in the user from a characteristic determining device, and a processor contained in the housing and coupled to the communication system for processing the data indicative of the determined concentration of the analyte in the user and controlling the infusion device. In particular embodiments, the infusion device is sized smaller than 6 inches long by 4 inches wide by 1 inch thick.

The infusion device may further include a bolus estimator used in conjunction with the processor for calculating an estimated amount of fluid to be infused into the body of the user based upon the received data indicative of the determined concentration of the analyte in the user and a target concentration of the analyte in the user, and an indicator to indicate when the estimated amount of fluid to be infused has been calculated. The system may determine the concentration of one of any variety of analyte types including, but not limited to, oxygen, blood, temperature, lactase, pH, implantable, and the like. Additionally, the infusion device may include a user input device, such as keys, buttons, or the like, for inputting an estimate of a material to be ingested by the user, and the bolus estimator may include the capability to calculate the estimated amount of fluid to be infused into the body of the user based upon the inputted estimate of the material to be ingested by the user. The infusion device may also include a memory for storing the data indicative of the determined concentration of the analyte in the user received by the infusion device communication system from the determining device communication system.

In still further alternative embodiments, the characteristic determining device is a BG measurement device and may use samples from body fluids other than blood, such as interstitial fluid, spinal fluid, saliva, urine, tears, sweat, or the like. In yet other alternative embodiments, other measurement devices may be utilized to determine the concentrations, levels, or quantities of other characteristics, analytes, or agents in the user, such as hormones, cholesterol, oxygen, pH, lactate, heart rate, respiratory rate, medication concentrations, viral loads (e.g., HIV), or the like. In still other alternative embodiments, other fluids may be delivered to the user, such as medication other than insulin (e.g., HIV drugs, drugs to treat pulmonary hypertension, iron chelation drugs, pain medications, and anti-cancer treatments), chemicals, enzymes, antigens, hormones, vitamins, or the like. Particular embodiments are directed towards the use in humans; however, in alternative embodiments, the infusion devices may be used in animals. For pain management, a bolus function may be set up as a Patient Controlled Analgesic (PCA) function for customized delivery or the user may press a preset bolus button several times.

In other embodiments, the characteristic determining device is a BG meter that determines BG level and the infusion device is an insulin infusion pump. The BG meter communicates the measurement of BG to the infusion pump device to determine the amount of insulin for delivery to the user. In alternative embodiments, the BG measurement device may be a continuous glucose measurement system, a hospital hemacue, an automated intermittent blood glucose measurement system, and the like, and/or the BG measurement device may use other methods for measuring the user's BG level, such as a sensor in contact with a body fluid, an optical sensor, a RF sensor, an enzymatic sensor, a fluorescent sensor, a blood sample placed in a receptacle, or the like. The BG measurement device may generally be of the type and/or include features disclosed in U.S. patent application Ser. No. 09/377,472 filed Aug. 19, 1999 and entitled "Telemetered Characteristic Monitor System and Method of Using the Same," Ser. No. 09/334,996 filed Jun. 17, 1999 and entitled "Characteristic Monitor with a Characteristic Meter and Method of Using the Same," Ser. No. 09/487,423 filed Jan. 20, 2000 and entitled "Handheld Personal Data Assistant (PDA) with a Medical Device and Method of Using the Same," and Ser. No. 09/935,827 filed Aug. 23, 2001 and entitled "Handheld Personal Data Assistant (PDA) with a Medical Device and Method of Using the Same," which are herein incorporated by reference. Such BG measurement devices may be adapted to be carried by the user, for example, in the hand, on the body, in a clothing pocket, attached to clothing (e.g., using a clip, strap, adhesive, or fastener), and the like. In particular embodiments, the BG measurement device is sized smaller than 6 inches long by 4 inches wide by 1 inch thick.

In alternative embodiments of the invention, the BG meter may be integrated into the controller device housing, as shown in FIG. 2, where the controller device housing 15 includes a BG meter receptacle 20. The controller device 10 includes a housing 15 adapted to be carried by the user, a BG meter receptacle 20 coupled to the housing 15 for receiving and testing BG level from the user to determine a concentration of the BG in the user. A BG test strip 25 that holds a user's blood sample is inserted into the BG meter receptacle 20 for testing by the controller device 10. In variations, the controller device 10 may have a cartridge-like mechanism which loads and presents the strip for testing and then ejects it. The controller device 10 has a display 30 on the housing 15 to show information requested by the user or an instructed act that was undertaken by the infusion device, such as for example, determined concentration of blood glucose levels, BG trends or graphs, such as described and disclosed in U.S. patent application Ser. No. 10/624,177, entitled "System for Monitoring Physiological Characteristics," which is herein incorporated by reference. The display 30 may further include a dedicated backlight 35 to facilitate viewing. The backlight 35 may be a user programmable multi-color backlight that additionally performs the function of a visual indicator by flashing colors appropriate to the level of an alert or alarm. The backlight 35 may also have variable intensity (automatic or manual) to preserve the battery power and improved viewing. The controller device 10 includes a keypad 40 on which various input devices, such as keys, buttons, or the like, are located. The keypad buttons 45*a*, 45*b*, 45*c*, and 45*d* are used by the user to select options and/or input information.

The power of the controller device and of the other various devices discussed herein may be provided from a battery. The battery may be a single use or a rechargeable battery. Where the battery is rechargeable, there may be a connector or other interface on a device to attach the device to an electrical outlet, docking station, portable recharger, or so forth to recharge the battery while in the device. It is also possible that a rechargeable battery may be removable from the device for recharging outside of the device, however, in some cases, the rechargeable battery may be sealed into the housing of the device to create a more water resistant or waterproof housing. The devices may be adapted to accommodate various battery types and shapes. In further embodiments, the devices may be adapted to accommodate more than one type of battery. For example, a device may be adapted to accommodate a rechargeable battery and, in the event of battery failure or other need, also adapted to accommodate a readily available battery, such as a AA battery, AAA battery, or coin cell battery.

Figure 3:
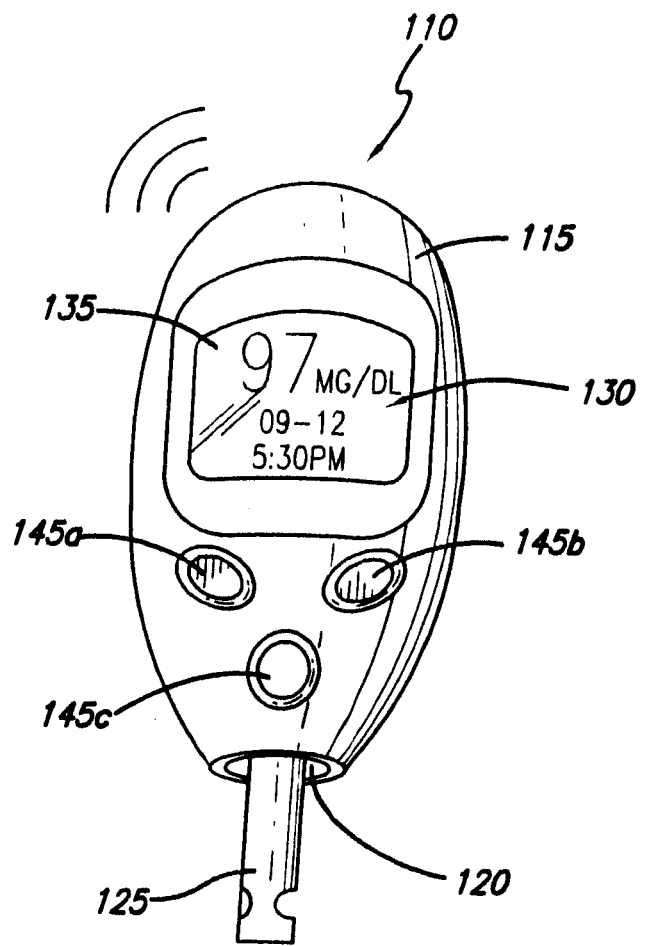
FIG. 3 is a front view of a blood glucose meter integrated into a controller device housing according to another embodiment of the invention.

In FIG. 3, another embodiment of a controller device is shown. Again, the controller device 110 includes a housing 115 adapted to be carried by the user, and a BG meter receptacle 120 coupled to the housing 115 for receiving and testing the BG level from the user to determine a concentration of the BG in the user. A BG test strip 125 that holds a user's blood sample is inserted into the BG meter receptacle 120 for testing by the controller device 110. The controller device 110 has a display 130 on the housing 115 to show information requested by the user or an instructed act that was undertaken by the infusion device, such as for example, determined concentration of blood glucose levels, graphs of blood glucose level trends or fluid delivery information. The display 130 may include a dedicated backlight 135 to facilitate viewing. The controller device 110 includes a few input devices, such as keys, buttons, or the like, on the housing 115. The housing buttons 145*a*, 145*b*, and 145*c* are used by the user to select options and/or input information.

Figure 4A:
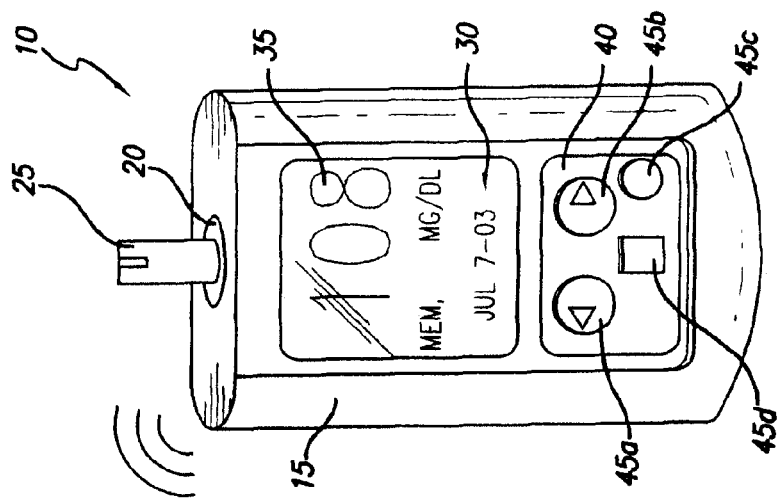
FIG. 4A is a front view of a blood glucose meter integrated into a controller device housing communicating with an infusion device according to an embodiment of the invention.
Figure 4A:
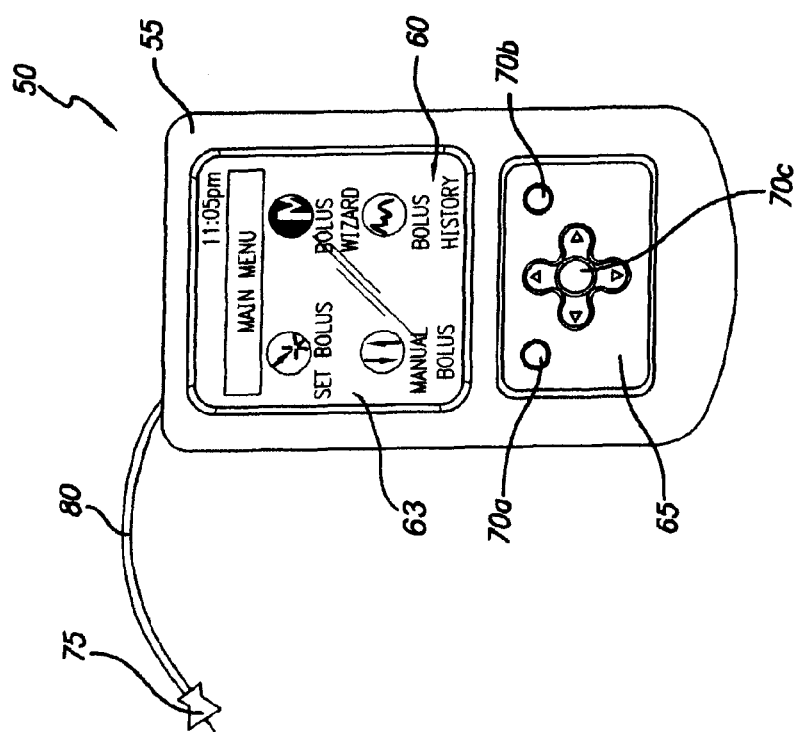

FIG. 4A illustrates an embodiment of an infusion system that includes an infusion device 50, and further includes a controller device integrated with a BG meter 10, where both share one housing. The controller device 10 communicates to the infusion pump device 50 through a wireless method, for example RF signals. The controller device 10 senses and determines the concentration of BG level of a patient and controls the infusion device 50 according to the measurements. This substantially reduces, if not eliminates, calculations on the part of the patient. In particular embodiments, the infusion device 50 includes a housing 55 adapted to be carried by the user. On the housing 55 there is included a display 60 that, like the BG meter display 30, shows information requested by the user or an instructed act that was undertaken by the infusion device 50. The infusion device 50 may not include a display, but in that case there should be a suspend/resume input and an action input for safety reasons. The BG meter display 30 shows information according to communications sent to the controller device 10 from the infusion device 50. At any moment, the display 60 of the infusion device 50 may show substantially the same information as shown on the controller device display 30. The two displays may mimic one another so that the user may choose to conveniently view the selected information from the controller device 10 rather than the infusion device 50, which is usually attached to the user's body through the infusion set 75. The infusion device 50 delivers fluid from within the housing 55, through tubing 80, into the infusion set 75, and into the user's body at an infusion site.

In embodiments where the infusion device 50 does include a display, the display 60 may further include a dedicated backlight 63 to facilitate viewing. The backlight 63 may be a user programmable multi-color backlight that additionally performs the function of a visual indicator, which may flash and/or turn to a color, e.g., yellow or red, when an alert or alarm takes place. The backlight 63 may also have variable intensity (automatic or manual) to preserve the battery power and provide improved viewing. Further included on the infusion device 50 is a keypad 65 with various input devices, such as the keypad buttons 70*a*, 70*b*, and 70*c* illustrated in the figure.

Figure 4B:
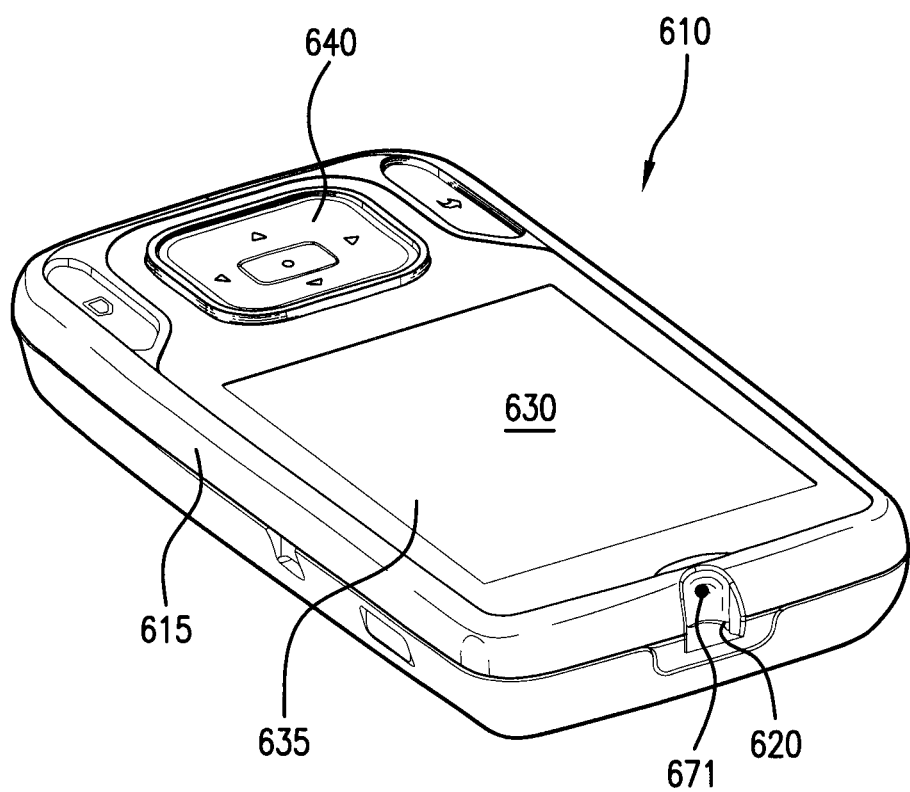
FIG. 4B is a perspective view of a controller device according to another embodiment of the invention.

FIG. 4B shows another embodiment of a controller device 610. As in the embodiments described previously, the controller device 610 includes a housing 615 adapted to be carried by the user, and a BG meter receptacle 620 coupled to the housing 615 for receiving and testing BG levels from the user to determine a concentration of the BG in the user. A BG test strip 625 that holds a user's blood sample is inserted into the BG meter receptacle 620 for testing by the controller device 610. The controller device 610 has a display 630 on the housing 615 to show information requested by the user or an instructed act that was undertaken by an infusion device, such as, for example, the determined concentration of blood glucose levels, graphs of blood glucose level trends, or fluid delivery information. The display 630 may include a dedicated backlight 635 to facilitate viewing. The controller device 610 includes a keypad 640, which may be used by the user to select options and/or input information. In addition, or alternatively, option selection and/or data entry may be performed by means of a touch screen via the display 630.

The controller device 610 also includes an illuminator 671 to assist users who might experience difficulty with proper placement of the test strip 625 into the BG meter receptacle 620 in low-light environments. In order to illuminate the receptacle 620 and/or the test strip 625, the illuminator 671 may be generally disposed within the vicinity of the BG meter receptacle 620. Thus, in FIGS. 4B and 4C, the illuminator is shown to be located just above the BG meter receptacle 620; however, this is by way of illustration and example only, and the illuminator 671 may be located at other locations relative to the receptacle 620.

Figure 4C:
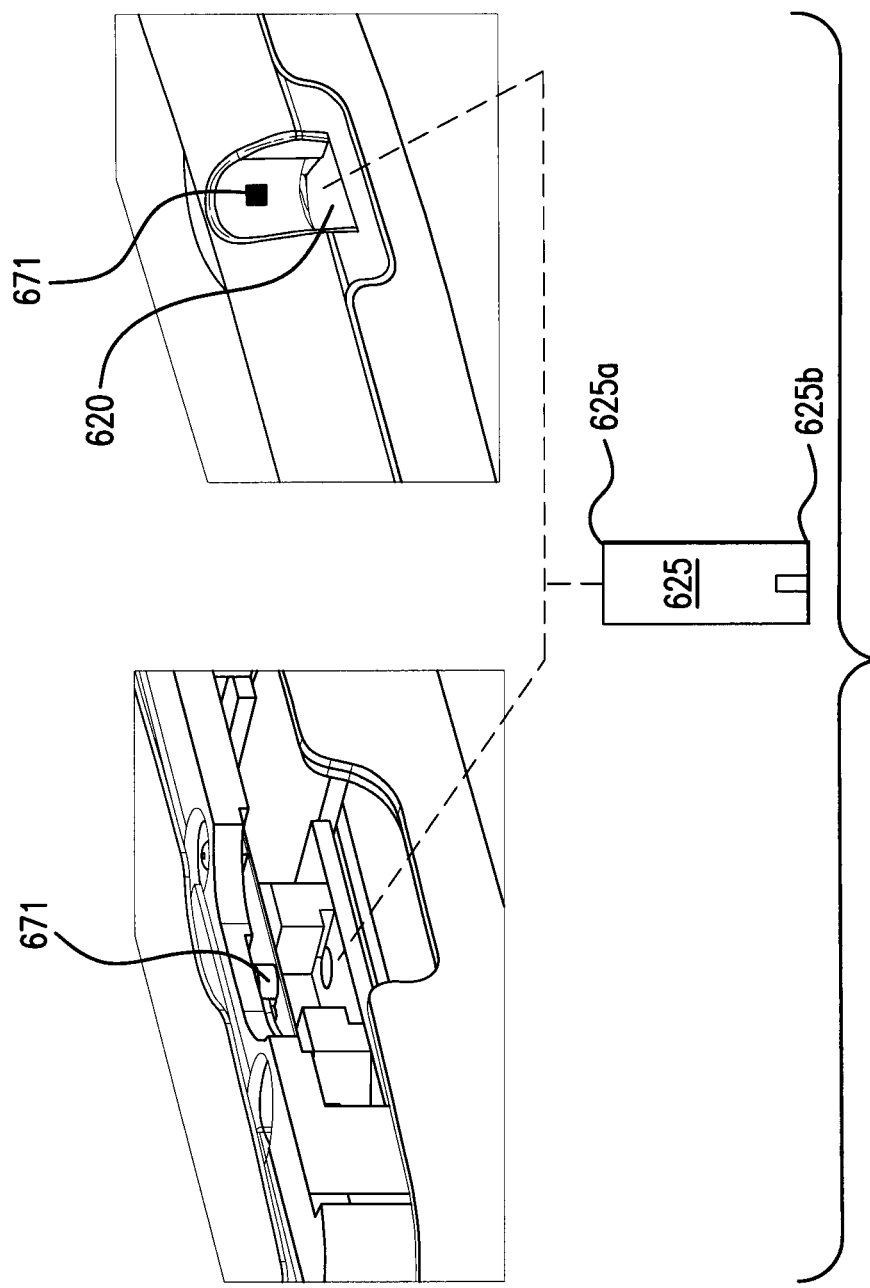
FIG. 4C shows a test-strip receptacle and associated test strip for a blood glucose meter integrated into the housing of the controller device shown in FIG. 4B.

As shown in FIG. 4C, the test strip 625 has a first end 625*a* which is inserted into the receptacle 620, and a second, free end 625*b*. In practice, it may be desirable to have the illuminator 671 illuminate an area that covers not only the opening of the receptacle 620, but also the free end 625*b* of the test strip 625 when the test strip is completely inserted into the receptacle, as the free end 625*b* is the point at which blood contacts the strip. To this end, in embodiments of the invention, the illuminator 671 is configured to project its light forward for a pre-determined distance (e.g., 20 mm) beyond the opening of the receptacle 620 to ensure that the free end 625*b* of the test strip is illuminated when the test strip is fully inserted into the receptacle.

In certain embodiments, the illuminator 671 may be a light-emitting diode (LED) and may be configured to provide various levels of light intensity. For example, the illuminator 671 may provide low-intensity illumination when the backlight 635 of the controller device display 630 is on. On the other hand, the illuminator may provide high-intensity illumination when the test strip 625 is inserted into the receptacle 620. Depending on the specific application, the low-intensity illumination may fall, e.g., within a range of about 2 to about 5 millicandelas at 110° F., and the high-intensity illumination may fall within a range of about 40 to about 50 millicandelas at 110° F. The LED may emit white light, although other colors of lighting may also be used.

The illuminator 671 may be configured to be activated automatically upon insertion of the test strip 625. Additionally, and/or alternatively, the controller device 610 may include an illuminator on/off button, key, or similar mechanism for selective activation/deactivation by the user. In this regard, the illuminator 671 may be used to illuminate the patient's lancet site when taking a BG reading. Similarly, the illuminator may be used to illuminate the patient's site to not only enhance proper placement, but also locate and identify skin irritation, leakage, and the like. In embodiments of the invention, the controller device 610 may include a light sensor for measuring ambient light. In such embodiments, the illuminator 671 may be activated only when the measured light level falls below a pre-determined intensity. Thus, the illuminator 671 may be configured to be activated, e.g., only at night, or only in a dark room, etc., thereby helping to preserve power. The light sensor may be of the type that is generally known in the art, such as, e.g., those used in low-power battery-operated devices. The controller device 610 may communicate and interact with the infusion device 50 as shown and described in connection with FIG. 4A.

Figure 4D:
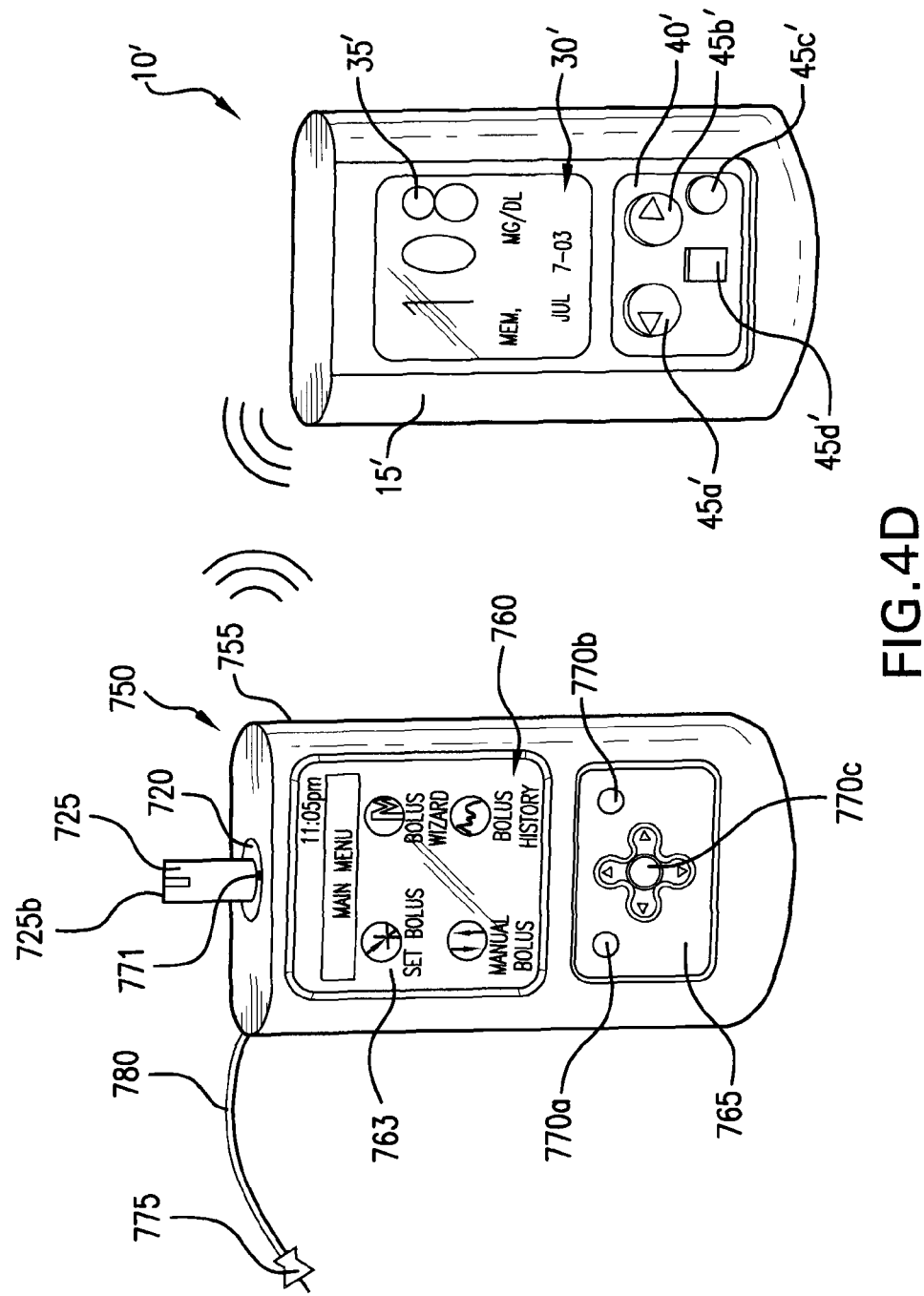
FIG. 4D is a front view of an infusion device, including a blood glucose meter integrated into a single housing, communicating with a controller device according to an embodiment of the invention.

FIG. 4D shows an embodiment of an infusion system in which a BG meter is integrated into the infusion device 750, which communicates with a controller device 10' through a wireless method, such as, e.g., RF signals. The infusion device 750 senses and determines the concentration of BG level of a patient, and then acts in accordance with the measurements. As in previously-described embodiments, this substantially reduces, if not eliminates, calculations on the part of the patient. In particular embodiments, the infusion device 750 includes a housing 755 adapted to be carried by the user. On the housing 755 there is included a display 760 that shows information requested by the user or an instructed act that was undertaken by the infusion device 750. The infusion device 750 may not include a display, but in that case there should be a suspend/resume input and an action input for safety reasons. The controller device display 30' shows information according to communications sent to the controller device 10' from the infusion device 750. At any moment, the display 760 of the infusion device 750 may show substantially the same information as shown on the controller device display 30'. The two displays may mimic one another so that the user may choose to conveniently view the selected information from the controller device 10' rather than the infusion device 750, which is usually attached to the user's body through the infusion set 775. The infusion device 750 delivers fluid from within the housing 755, through tubing 780, into the infusion set 775, and into the user's body at an infusion site.

It is noted that, in FIG. 4D, the controller device 10' includes substantially the same components and structural elements, and performs substantially the same functions, as the controller device 10 shown in FIG. 2, with the exception that controller device 10' does not include an integrated BG meter, thereby eliminating the need for a receptacle 20 to receive a test strip 25. Thus, the housing 15', the display 30', and the backlight 35' (when present) may correspond, respectively, to the housing 15, the display 30, and the backlight 35. Moreover, the keypad 40' and keypad buttons 40a', 40b', 40c', 40d' may correspond, respectively, to keypad 40 and keypad buttons 40a, 40b, 40c, 40d. Alternatively, the keypad 40', the keypad buttons 40a', 40b', 40c', 40d', and/or the display 30' may be supplemented or replaced with the keypad 640 shown in FIG. 4B and/or a touch screen.

Returning to the infusion device 750 of FIG. 4D, in embodiments where the infusion device does include a display, the display 760 may further include a dedicated backlight 763 to facilitate viewing. The backlight 763 may be a user programmable multi-color backlight that additionally performs the function of a visual indicator, which may flash and/or turn to a color, e.g., yellow or red, when an alert or alarm takes place. The backlight 763 may also have variable intensity (automatic or manual) to preserve the battery power and provide improved viewing. Further included on the infusion device 750 is a keypad 765 with various input devices, such as the keypad buttons 770a, 770b, and 770c illustrated in the figure.

The infusion device 750 also includes a BG meter receptacle 720 coupled to the housing 755 for receiving and testing BG levels from the user to determine a concentration of the BG in the user. A BG test strip 725 that holds a user's blood sample is inserted into the BG meter receptacle 720 for testing by the infusion device 750. The infusion device 750 also includes an illuminator 771 to assist users who might experience difficulty with proper placement of the test strip 725 into the BG meter receptacle 720 in low-light environments. In order to illuminate the receptacle 720 and/or the test strip 725, the illuminator 771 may be generally disposed within the vicinity of the BG meter receptacle 720. Thus, in FIG. 4D, the illuminator is shown to be located just above the test strip 725; however, this is by way of illustration and example only, and the illuminator 771 may be located at other locations relative to the receptacle 720.

The test strip 725 has a first end (not shown) which is inserted into the receptacle 720, and a second, free end 725b. In practice, it may be desirable to have the illuminator 771 illuminate an area that covers not only the opening of the receptacle 720, but also the free end 725b of the test strip 725 when the test strip is completely inserted into the receptacle, as the free end 725b is the point at which blood contacts the strip. To this end, in embodiments of the invention, the illuminator 771 is configured to project its light forward for a pre-determined distance (e.g., 20 mm) beyond the opening of the receptacle 720 to ensure that the free end 725b of the test strip is illuminated when the test strip is fully inserted into the receptacle.

In certain embodiments, the illuminator 771 may be a light-emitting diode (LED) and may be configured to provide various levels of light intensity. For example, the illuminator 771 may provide low-intensity illumination when the backlight 763 of the infusion device display 760 is on. On the other hand, the illuminator may provide high-intensity illumination when the test strip 725 is inserted into the receptacle 720. Depending on the specific application, the low-intensity illumination may fall, e.g., within a range of about 2 to about 5 millicandelas at 110° F., and the high-intensity illumination may fall within a range of about 40 to about 50 millicandelas at 110° F. The LED may emit white light, although other colors of lighting may also be used.

The illuminator 771 may be configured to be activated automatically upon insertion of the test strip 725. Additionally, and/or alternatively, the infusion device 750 may include an illuminator on/off button, key, or similar mechanism for selective activation/deactivation by the user. In this regard, the illuminator 771 may be used to illuminate the patient's lancet site when taking a BG reading. Similarly, the illuminator may be used to illuminate the patient's site to not only enhance proper placement, but also locate and identify skin irritation, leakage, and the like. In embodiments of the invention, the infusion device 750 may include a light sensor for measuring ambient light. In such embodiments, the illuminator 771 may be activated only when the measured light level falls below a pre-determined intensity. Thus, the illuminator 771 may be configured to be activated, e.g., only at night, or only in a dark room, etc., thereby helping to preserve power. The light sensor may be of the type that is generally known in the art, such as, e.g., those used in low-power battery-operated devices.

Figure 5:
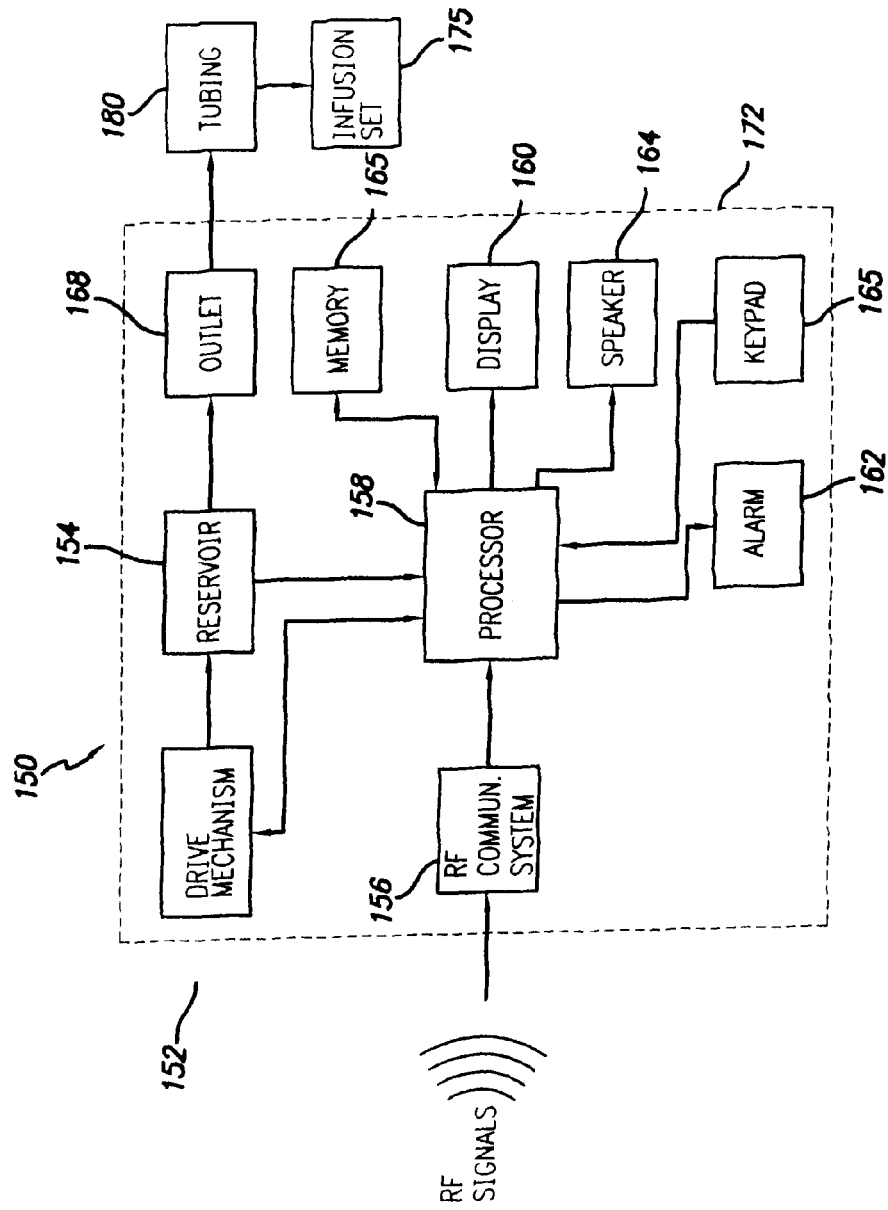
FIG. 5 is a block diagram of an RF communication system in an infusion device according to an embodiment of the invention.

FIG. 5 provides a block diagram of the infusion device 150. The infusion device 150 includes a drive mechanism 152 contained in the housing 172 and operatively coupled with a reservoir 154 containing the fluid for infusing the fluid into the body of the user, a communication system 156 contained in the housing 172 for receiving the communication from the controller device including data indicative of the determined concentration of the BG in the user from the BG meter, and a processor 158 contained in the housing 172 and coupled to the communication system 156 for processing the received communications and controlling the infusion device 150. The fluid is delivered from the reservoir 154 through an outlet 168 in the housing 172 and into the user's body via the tubing 180 and infusion set 175. The infusion device 150 may further include an indicator displayed on the display 160 to indicate when the estimated amount of fluid to be infused has been calculated. Additionally, the infusion device 150 may include one or more user input device(s), such as keys, buttons, and the like, for inputting an estimate of a material to be ingested by the user, and the estimated amount of fluid to be infused into the body of the user may be based upon this inputted estimate of material to be ingested. A bolus estimator may be used in conjunction with the infusion device processor for estimating the appropriate amount of fluid to be infused into the body of the user. There may be included a keypad 165 on which the one or more input device(s) are located. The infusion device 150 may also include a memory 166 for storing the data received by the infusion device communication system 156 from the controller device communication system.

In further embodiments, a speaker 164 is included to provide an alternative mode of communication. In an embodiment, the infusion device 150 may display a message that states "move nearer to pump" when the BG meter or controller device senses that the communication with the infusion device 150 is weak or interrupted. A similar message may be displayed if the BG meter or controller device senses some type of problem or malfunction. Alternatively, an alarm 162 may alert the user of any problem or malfunction by vibrating, emitting warning sounds, flashing light, and the like. In further embodiments, the infusion device 150 may provide other functions that show a variety of other displays, for example, when the last bolus was administered, when the last alarm occurred, when the last finger stick was taken, past trends, all alarms that occurred in a time period, calibrations, meals, exercise, bolus schedules, temporary basal delivery, and the like. Whenever a bolus is being delivered, the infusion device 150 can send a message every time a tenth of a unit, or some specified amount, is delivered.

Figure 6A:
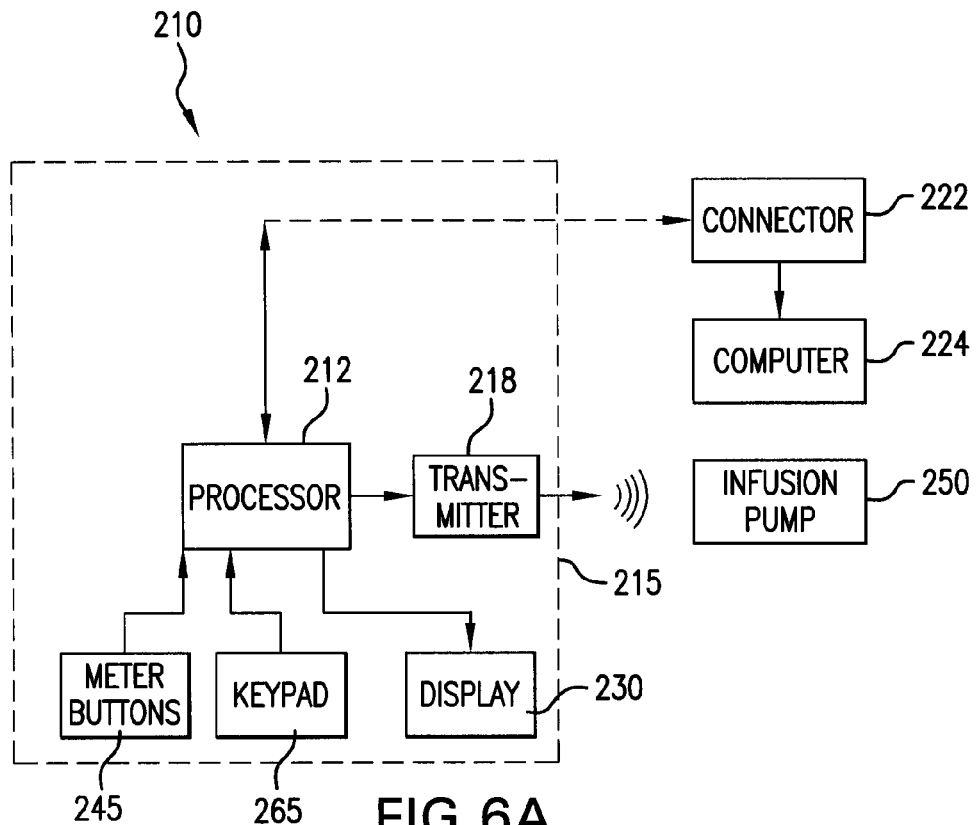
FIG. 6A is a block diagram of a controller device according to an embodiment of the invention.
Figure 6B:
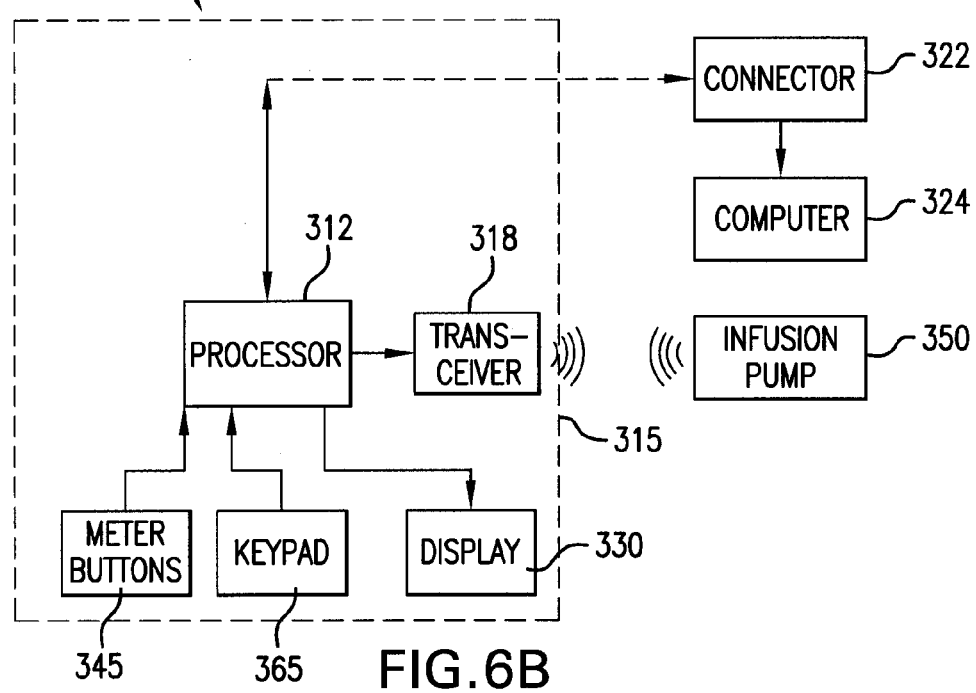
FIG. 6B is a block diagram of a controller device according to an embodiment of the invention.

As seen in FIGS. 6A and 6B, the controller device 210, 310 includes a housing 215, 315 adapted to be carried by the user. A processor 212, 312 contained in the housing 215, 315 is adapted to process data and commands inputted by the user, and a transmitter 218 (or a transceiver 318 (as shown in FIG. 6B)) contained in the housing 215, 315 and coupled to the processor 212, 312 transmits such communications, including data indicative of the determined concentration of the BG in the user, to the infusion device 250, 350. In further embodiments, the controller device 210, 310 may be integrated with a BG meter in one housing, which has a lancing device and receptacle for BG test strips, for obtaining a BG sample from the user.

The controller device 210, 310 may communicate with a remote station, such as a computer 224, 324 through a data transfer system, using a type of communication connector 222, 322 that couples the controller device 210, 310 to the computer 224, 324 and allows the data downloading. Alternatively, communication may be by wireless methods, such as RF, IR, BLUETOOTH (as one type of frequency-hopping spread spectrum communication technology), or other wireless methods. Data may be downloaded via the RF telemetry in the same manner as data is transferred from the controller device 210, 310 to the infusion pump device 250, 350. The transmitter 218 (or a transceiver 318 (as shown in FIG. 6B)) converts RF signals into compatible electrical pulses that may be subsequently sent through a serial port to a specified destination. Data, including software upgrades and diagnostic tools, may also be downloaded via RF telemetry, or any other wireless or wired method, from a remote station, such as the computer 224, 324 to the infusion device 250, 350. Other remote stations include, but are not limited to, a hospital database, a cellular telephone, a PDA, a smart phone or internet. For example, a cellular phone may be used as a conduit for remote monitoring and programming. In one embodiment, the controller device may be configured so as to have cellular telephone capabilities. In further embodiments, the controller device and/or the other devices with display may be capable of providing PDA functions as well, removing the need for patients to carry separate PDA devices.

The controller device 210, 310 includes on the housing a display 230, 330 that may mimic the display on the infusion pump device 250, 350. The controller device display 230, 330 shows information according to communications sent to the controller device 210, 310 from the infusion device 250, 350. At any moment, the display of the infusion device 250, 350 may show substantially the same information as shown on the controller device display 230, 330. In some embodiments, whatever is shown on the infusion device 250, 350 corresponds to that shown and reflected on the display 230, 330 of the controller device 210, 310. In this manner, the user may more conveniently view what is being processed or acted upon in the infusion pump device 250, 350 without removing or adjusting the infusion pump device 250, 350 to view the display. In embodiments, the controller device 210, 310 may include one or more input device(s) 245, 345, such as keys, buttons, and the like, on a keypad 265, 365 so that all, or substantially all, viewing and data entry may be performed on the same device without moving the infusion pump device 250, 350.

Figure 7:
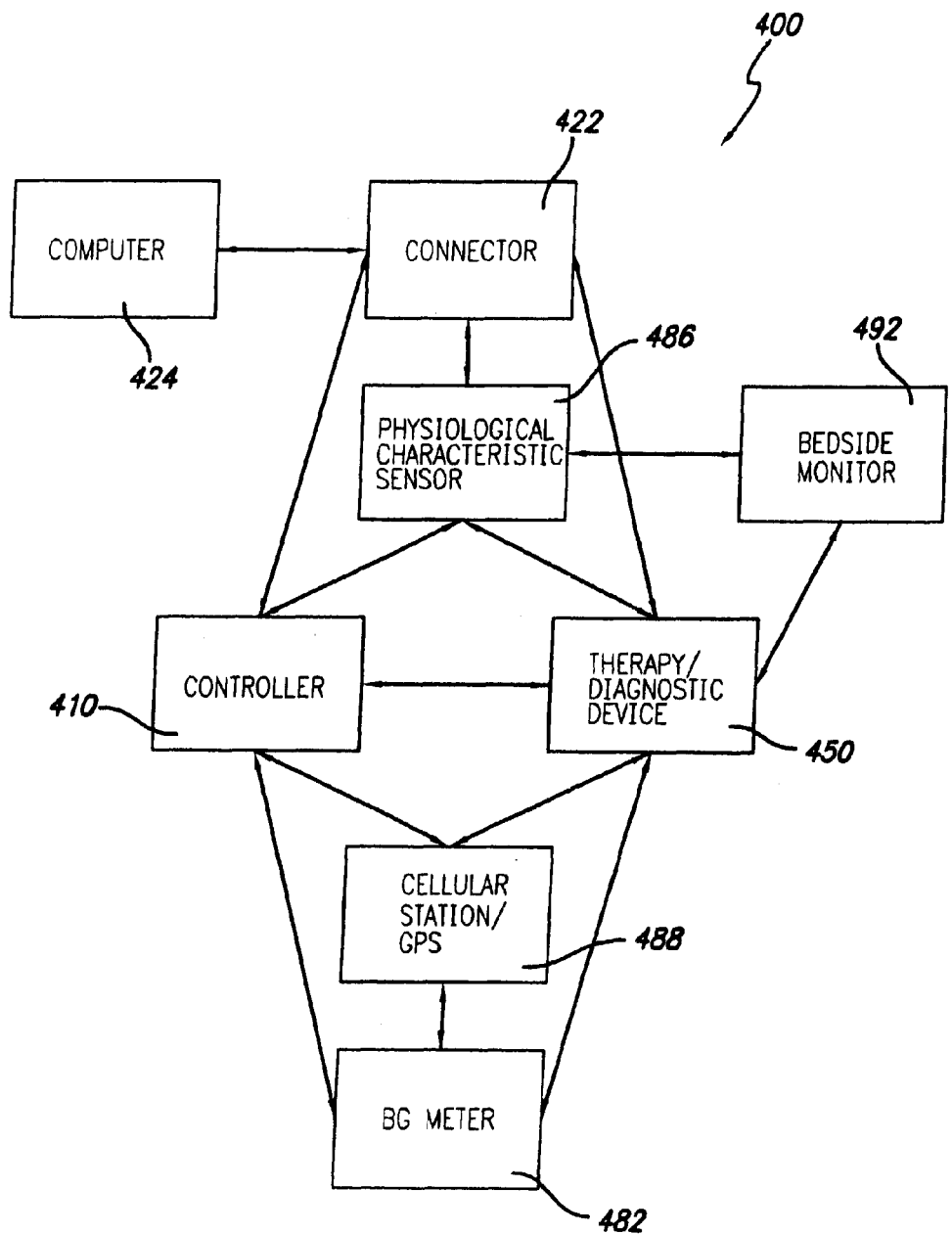
FIG. 7 is a block diagram of different communication paths within the infusion system according to an embodiment of the invention.

The infusion pump device 250, 350 and the controller device 210, 310 need to have substantially the same resolution or else the screen may not be presented correctly on the display. Another difficulty may be in properly displaying the scaling of graphs. This issue may be addressed by having the infusion pump device talk in an "ideal" screen, and not necessarily in its actual screen format. As shown in FIG. 7, the potential communication paths within embodiments of the infusion system are illustrated. The controller device 410 may serve as a translator between the infusion device 450 and the other components of the infusion system 400, such as a BG meter 482. For example, the controller device 410 may have the ability to determine how best to translate the infusion device's 450 description to the screen of the two displays. As can be seen, the infusion device 450 may communicate directly with the BG meter 482. In alternative embodiments, the resolution need not be the same, and the infusion device and/or controller can compensate for the resolution difference so that one or the other may utilize enhanced displays or a simple display depending on the devices and the needs of the user.

In some embodiments, the infusion system 400 may include multiple controllers that can communicate with one infusion device 450. In other embodiments, there is one controller device 410 communicating to one infusion device 450. The controller device may also be integrated into the infusion device in some embodiments. In an alternative embodiment, in addition to, or in place of, the controller device 410, the BG meter 482 may be integrated into the infusion device 450, sharing a single housing. In yet another embodiment, the BG meter 482 may be integrated into the controller device 410, sharing one housing, to both communicate with the infusion pump device 450. In this embodiment, the controller is separate from the infusion pump device. In this embodiment, the infusion device 450 serves as the central hub with most of the intelligence of the system 400. In yet another embodiment, the controller device 410 may be a key fob, in which case, the controller device 410 would serve simply as a virtual keyboard to input data and commands to the infusion device 450. Optional peripheral devices may include a physiological characteristic sensor device, such as a telemetered glucose monitoring system (TGMS) sensor. Alternatively, the sensor may be directly wired to a monitor/user interface. The TGMS sensor or physiological characteristic sensor 486 may provide for continuous BG monitoring. The physiological characteristic sensor 486 may also be linked to a bedside monitor 492 so that monitoring and programming of medication delivery may be performed remotely. In some embodiments, the infusion pump device does not include, nor need, a display. In this embodiment, a key fob may serve as a remote display. Other options for a remote display include, but are not limited to, cellular telephones, computer monitors, PDA's, smart phones, watch remotes, and the like. The infusion device 450 may further communicate with, and download data such as software upgrades and diagnostic tools from, a remote station like a computer 424 from a connector 422. Optionally, the infusion device 450 may also communicate with the controller device 410 through a station such as a cellular station 488 that includes GPS. In further embodiments, the connector 422 may have memory capability to transport data.

In the above embodiment, the control is maintained in the central hub and the infusion pump device 450 sends out most of the commands. The infusion device 450 also sends requests to receive specific data from the controller device 410. The controller device 410 and the infusion pump device 450 may communicate to one another by a connector 422, other wired methods or by wireless methods, such as RF, IR, BLUETOOTH (as one type of frequency-hopping spread spectrum communication technology), or other wireless methods. In other embodiments, the infusion pump device 450 may contain all or substantially all of the intelligence. The controller device 410 and the infusion device 450 may be limited in the amount of time that they communicate with one another to save power in the controller device 410. For example, RF communications may be minimized, such that the marriage between the infusion pump device 450 and controller device 410 occurs once. The information regarding the screens displayed is sent to the controller device 410, and when the infusion pump device 450 needs to display a screen, it sends a screen number to the controller device 410. In the case of screen displays, if the data being sent is fixed, then the screen can be simply displayed. If the data is variable, then the variable data is sent with the screen to the infusion pump device 450. The screen is then displayed based on a combination of the fixed screen information and the variable data. Exchange IDs, strings to be displayed, and foreign languages are among data that may be sent from the controller device 410. Further commands that may be sent from the infusion pump device 450 include, among other commands, a command to show a specific screen on the controller device 410, a command for displaying requested information on the screen, a command for showing the rules for the input devices, a command for showing the intelligence about that screen type (e.g., menus, data entries, etc.), and the like. The devices may all send diagnostic information to each other, and particularly to the controller device, so that the user may see if anything is going wrong with any of the devices.

Figure 8:
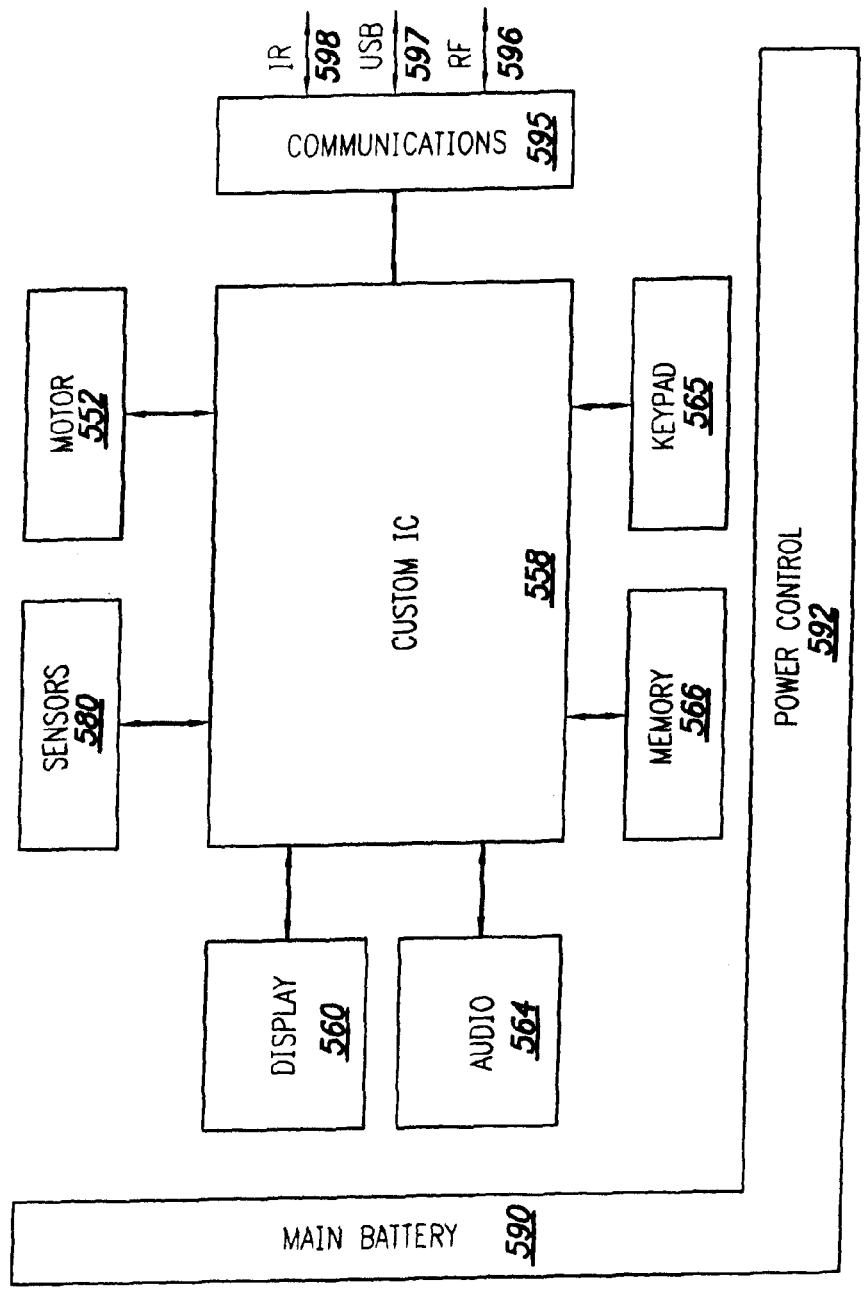
FIG. 8 is a diagram of the electronics architecture of a controller device according to an embodiment of the invention with a custom integrated circuit.

FIG. 8 shows an electronics architecture according to an embodiment of the invention with a custom integrated circuit ("custom IC") 558 as the processor. This architecture can support many of the devices discussed herein, for example the controller device, the infusion device, the characteristic determining device, a BG meter, or any combination of the above. The custom IC 558 is in communication with a memory 566, keypad 565, audio devices 564 (such as speakers or audio electronic circuitry such as voice recognition, synthesis or other audio reproduction), and a display 560. Where there is a drive mechanism in a device that includes infusion functions, the custom IC 558 is in communication with a motor 552 or motor drive circuitry or other means of delivering fluids or therapy via an electro-mechanical means. Where there are one more sensors included in the device, or in communication with the device (such as a characteristic determining device or a device which includes a characteristic determining function), the custom IC 558 is in communication with the sensors 580. The electronics architecture further may include a communications block 595 in communication with the custom IC 558. The communications block 595 may be adapted to provide communication via one or more communications methods, such as RF 596, a USB 597, and JR 598. In further embodiments, the custom IC 558 may be replaced by electronic circuitry, discrete or other circuitry, with similar functions.

The electronics architecture may include a main battery 590 and a power control 592. The power control 592 may be adapted to give an end of battery warning to the user, which can be predicted based on the type of battery used or can be calculated from the power degradation of the battery being used. However, in certain embodiments it is not necessary to know the type of battery used to create an end of battery warning. Various battery types, such as rechargeable, lithium, alkaline, etc., can be accommodated by this design. In certain embodiments, the electronics architecture includes a removable battery and an internal backup battery. Whenever a new removable batter is inserted, the internal backup battery will be charged to full capacity and then disconnected. After the removable battery has been drained of most of its energy, it will be switched out of the circuit and the internal backup battery will be used to supply power to the device. A low battery warning may then be issued. The internal backup battery may be rechargeable. In further embodiments, a supercap, for example, is used to handle the peak loads that the rechargeable internal battery could not handle directly, because it has sufficient energy storage. This method also allows the use of any type of removable battery (alkaline, lithium, rechargeable, etc.) and partially drained batteries. Depending on use, the backup battery may allow the device to operate for at least one day after the removable battery has been drained or removed. In further embodiments, a microprocessor measures the charge states and control switches for removable and internal backup batteries.

In certain embodiments, the controller device has no user settings and very little memory, because all, or substantially all, needed data and instructions will be sent to the controller device by the infusion pump device. Thus, the functions are all, or substantially all, contained on the infusion pump device in such embodiments.

In alternative embodiments, the infusion pump device may include expanded capabilities, such as color on the display screens, and more graph options that can present more detailed graphs. For example, there may be included a graph called "mobile day" where the BG levels of the user for the past five days may be shown as overlapping graphs. The mobile day graph allows the user to see the trend in BG level changes during those days, and aids the user in better controlling the insulin delivery according to the trends that appear for specific times of each day.

The BG meter may also include expanded capabilities, such as for example, voice synthesis, voice activation, polyphonic speakers for the vision impaired, and plugs on the BG meter for headphones. Likewise, the controller device may also be configured to provide these expanded capabilities.

As described above, the controller device may be integrated with the BG meter in some embodiments. In those embodiments, the input keys and the display will all, or substantially all, be included on the controller device. The BG meter may also be separate from the controller device and may talk directly to a sensing device, such as a TGMS sensor. The TGMS sensor is inserted into the subcutaneous tissue of the user to read body fluids, and allows for continuous blood glucose monitoring. The readings are used in conjunction with the BG level determined by the BG meter to continuously monitor BG levels through extrapolating the BG measurements. This embodiment would be compatible with users that do not have an infusion pump device, in which case, there is a need for the ability to talk directly to the TGMS sensor without talking to the infusion pump device.

If the BG meter talks to the TGMS sensor then the TGMS sensor may broadcast the data received from the BG meter to the infusion pump device and the controller device. In some embodiments, the infusion pump device will always send the data to the controller device. In the case that the controller device does not receive the information from the infusion pump device, it will assume that the infusion pump device has not received the data and will communicate the value to infusion pump device. In other embodiments, the infusion pump device, controller device and TGMS sensor maintain a three-way communication with one another, and have the ability to check the contacts between one another. In still further embodiments, the system is set up to automatically call for assistance when analytes reach a certain level. The call may include a GPS location.

In an embodiment of the present invention, the graph displayed on the controller device may display information regarding boluses, finger sticks, exercise, meals and the like. In one embodiment, the graph displayed has eight segments, representing different limits and an actual BG line. In other embodiments, the graphs may include additional time spans for which to show the varying BG levels. For example, the embodiments may include a 3 hour, 6, 12, and 24 hour graphs. Additional features of the graphs may include the ability to zoom in or out of the graph. There may be included an ESC key that will allow the user to return to the last scale. Other options may allow the user to focus on specific positions on a graph. In yet another feature, the user can select the resolution in which to view the graph.

In a situation where the infusion pump device and the controller device are out of sync, e.g., the graph on the pump and the graph on the controller device do not look substantially the same, there needs to be a way to resynchronize the two components if something goes wrong. For example, if finger stick values do not both have current finger stick values, then the graphs for the controller device and the infusion pump device would be different.

There also may be some type of positive mechanism for the controller device if the communication between the controller device and the pump is interrupted. For example, the mechanism may have the controller device stop displaying its graph in a "time-out" phase for the time the infusion pump device screen is absent or no more data is entered by the user for a period of time. In this case, the infusion pump device operates on the last data that the infusion pump device sent to the controller device to display. In an embodiment, the controller device will display an idle screen during the time-out phase and while the communication between the infusion pump device and the controller device is re-established. The idle screen may remain until the next action is selected by the user. After the time-out phase, the user may press a key to start up the communication again. Once a key is pressed, the controller device will process the key data and the screen will be displayed. The controller device may periodically send signals to the pump to see if it is still active on the screen.

In alternative embodiments, there will be a positive confirmation requested prior to displaying graphs. For example, the graphs may be shown in bitmap packets (e.g., bit-by-bit), and if the user will be getting a large number of packets of data, for example 15 packets of data, to show the graph, the user may opt not to confirm. The data is passed from the controller device, which is programmed to display the data, to the infusion pump device. The controller device can operate in graphics description language where data is recognized by the controller device as instructing it on which position to put each line or color and the graphics display would handle determining the resolution that the graph would be displayed in. In some embodiments, the graph may be displayed in three-dimensional format.

The specific screens to be displayed may include fixed menus, partially variable menus, and variable menus. In fixed menus, the menus do not change depending on data. Therefore, they will always look substantially the same on the screen, and the controller device may be programmed to display them when requested. The fixed menus may be described as screen numbers. In this way, the controller device can easily request "screen 1" or "screen 2." In fixed menus, the text is defined once. There may also be menus where menu items appear and disappear depending on the current settings of the infusion pump device. These menus are considered partially variable menus because some data appear and disappear, and are not all fixed. For example, a program for bolus setup allows a user to change current bolus settings. Bolus set up menus involve variable information as well as fixed information. The values may be variable, but the main menu items (title of variables, etc.) will stay the same. Variable menus contain information that is completely variable, e.g., bolus history screen. Variable data is sent at the time of the screen display, and there is generally no fixed text. What is displayed in variable menus depend on what bolus action the user selects. The history screens resemble the menu screens in that the user cannot select and input any information with the history screen. Data entry screens, on the other hand, include multiple fields on a screen and can accept data selection and input by the user.

Different units may need to be switched dynamically depending on how the type of entry is communicated. The screens may also need to be able to display minimum and maximum values as well as time increments, to ensure precision of the display. The rules for this translation will be defined in the infusion pump device. Likewise, for a dual-wave bolus, there must be defined how the values interlock. Sensor high and low BG values also need to be interlocked (in some embodiments, these two values will be displayed in the same screen).

In one embodiment, communication between the infusion system components takes place when the user presses one or more keys to send data to the infusion pump device and, in response, the infusion pump device can relay to the controller device to instruct on what to display. Alternatively, the user may input data through scrolling down menus and selecting options. When the user prompts the controller device, for example by pressing an "ACT" button, the controller device will then tell the infusion pump what to do, e.g., deliver fluid to the user.

In its simplest form, the controller device is a display only, used to show a BG value and/or graph. In another simple form, the controller device embodies only a virtual keypad that may mimic exactly the buttons on the infusion device. When the user presses a key on the controller device, the controller device tells the infusion device what button was pressed—and the infusion device acts as if the button was pressed on the infusion device itself. Each component of the infusion system may be of different degrees of sophistication. For example, the controller device can range from a simple key fob with limited capabilities and with, for example, one or two keys to a complex device with memory, many keys and advanced graphing options. In a complex form, the controller device may embody all or substantially all of the intelligence that is present in the infusion device. In this form, the controller device could do all calculations, graphing functions, and other data input, output, and manipulation at the controller device. The controller device would then send data to the infusion device indicating what the controller device had done so that the infusion device could be put into the same state as the controller. It is possible for the controller device to have many different degrees of computing intelligence, so that few, none, many, or all computing may be done at the controller device. How much intelligence will be in the controller device may depend on battery life, size requirements, and so forth.

In further embodiments, the processor of the controller device has unique identification information, and the communication transmitted from the controller device to the infusion device further includes the unique identification information of the controller device processor such that the infusion device is capable of discerning whether the communication is intended for receipt by the infusion device. In yet further embodiments, the processor of the infusion device has unique identification information, and the communication transmitted from the controller device to the infusion device further includes the unique identification information of the infusion device processor such that the infusion device is capable of discerning whether the communication is intended for receipt by the infusion device.

Additionally, both the controller device and the BG meter may communicate over wireless networks. Some examples include RF, IR, spread spectrum communication, and frequency hopping communication. In further embodiments, there may be a "Listen Before Talk" scheme where the system selects the cleanest of allotted channels through which to communicate. Further examples include giving the controller device cellular telephone or pager capabilities. In the alternative, the communication may be wired, such as in hospital use. In a wired embodiment, there may be a tether physically connecting the infusion pump device to the controller device and/or BG meter. In yet another alternative, the controller device and the infusion pump device could be both wired and wireless—when wired, the two components communicate by wire, and when disconnected, the two components could operate through wireless communication.

In another wireless example, if the user has access to a computer network or phone connection, the user can open communication via the interne to obtain communications from, and send communications to, a nurse, parent, or anyone so desired. As discussed above, a transceiver may be used to facilitate data transfer between the PC and the infusion pump device. Such a communication may also be used by a party, other than the user, to control, suspend, and/or clear alarms. This embodiment could be very useful for a parent to monitor the infusion system of a child, or for a physician to monitor the infusion system of a patient. The transceiver may allow patients at home or clinicians in a hospital setting to communicate with the various components of the infusion system via RF telemetry. The transceiver may be used to download device information from the pump and sent to the PC when the transceiver is connected in to the serial port of the PC. In embodiments, the transceiver may derive its power from the PC when the two are connected. In this way, the transceiver conveniently does not require a separate power source. In another embodiment, a cellular phone may be used as a conduit for remote monitoring and programming. In yet other embodiments, the controller device with a BG meter may also act as a transceiver, which would eliminate an extra component.

In further embodiments, the controller device communication system is capable of being deactivated and reactivated. The controller device may include input devices, such as keys, buttons, and the like, for inputting commands, and the communication system of the controller device is capable of being deactivated in response to a first command from the user input device and being reactivated in response to a second command from the user input device. Alternatively, the communication system of the controller device may be automatically reactivated after a predetermined amount of time has elapsed or at a predetermined time of day.

In an embodiment of the present invention, the processor of the infusion device uses power cycling such that power is periodically supplied to the communication system of the infusion device until a communication is received from the controller device. When a communication is received from the controller device, the processor of the infusion device discontinues using power cycling so that the power is continuously supplied to the infusion device communication system. The infusion device processor may then resume using power cycling upon completing the receipt of the communication including the data indicative of the determined concentration of the analyte in the user from a BG meter communication system.

In yet another embodiment, the infusion system may include a bedside monitor. The monitor could communicate through the same avenues as the BG meter, the controller device, and the infusion pump device. The monitor could be used, as described above, to remotely alarm people other than the user, such as for example, parents, physicians, nurses, and the like. This would provide an extra layer of monitoring for the user, especially when the user is alone. In further embodiments, the system may be set up so that multiple devices are placed around the house. This would provide easy access to monitor the diabetic. Additionally, the parent will be able to obtain data to monitor a child user at home and when the parent is away. Such home monitors could be set to any mode preferred, for example, flashing lights, warning sounds like beeping, vibration, and the like. Other features may include a function that allows the remote user (parent, physician, nurse, etc.) to change and/or deliver a bolus from remote sites.

In an alternative, the controller device may be configured so as to have cellular telephone capabilities. The cellular network could provide a conduit for remote monitoring and programming. Additionally, the cellular network could be used to notify parents, physicians, or emergency services of alarms or alert states. A button may be included on the controller device and/or the infusion device to automatically alert a parent, physician, or emergency services when pressed. For example, a monitoring device may be built directly into a patient's cellular telephone so that in the case of a hypoglycemic event, an alarm or connection may be made to emergency services via the cellular telephone. In a further embodiment, GPS technology may also be built into the cellular telephone to allow easy location of the patient. Alternatively, GPS technology may be included in the controller device without cellular telephone technology. In other embodiments, the GPS technology may also be built into the infusion pump, BG meter or controller device.

The infusion system may be part of a closed-loop system, such as an implantable infusion system with a sensor system or an external infusion device with a sensor system. In such a system, there may be included safety nets, such as alarms and automatic shut-offs.

The alarms may be customized to specific user needs. The alarm may be set to flashing lights for the hearing impaired, or warning sounds and/or vibration for the vision impaired.

There could further be included headphones that can plug into the controller device for vision impaired to instruct the user on what to do in the case that an alarm goes off. The headphones could also be plugged into a MPEG player or the like. To avoid having the pump broadcast information, the alarms may be handled in a way where the user presses a button on the controller device. Alarms could also be included on the pump. There may further be included a turn-off option where, if there is a need to communicate with the controller, the user can choose a selection to turn off the controller. In further embodiments, there may be included a feature in any of the devices including an alarm where, when the device has sounded an alarm for a period of time and the user has not responded, the alarm will switch to a vibrate mode and/or will attempt to signal companion devices in the system to alarm the user.

It is noted that some users can be expected to have somewhat diminished visual and tactile abilities due to the complications from diabetes or other conditions. Thus, the display and buttons or other input devices may be configured and adapted to the needs of a user with diminished visual and tactile abilities. In alternative embodiments, the high level module (and/or the low level module) may communicate to the user by audio signals, such as beeps, speech or the like.

Other display settings may be customizable, including, but not limited to, the background, sounds, fonts, and wallpaper. There may be a children's mode, with limited features available so that a child cannot dispense too much medication at once. Different display features may be included in the module and/or may be downloaded from a computer. The high level module may have a memory with which to store customized settings or pump control. The memory may be of any type that is known in the art, such as a volatile or non-volatile memory. Both a volatile and non-volatile memory may be used, which can speed up operation of the pump. As an example, non-volatile memories that could be used in the invention include flash memories, thumb drives and/or memory sticks such as USB thumb drives, removable hard drives, and optical drives.

In some embodiments, the language that the controller device operates in may comprise several different languages, ranging from 1 language to about 40 languages and potentially more. To set language, data must be first initialized to modify the phrases and detail font that may be significantly different in one language as compared to another language. For example, some languages, such as Chinese, are read in vertical columns, from the right to the left, and thus, needs to be displayed in such manner. One way to overcome this complication in using different languages is to have fonts built into the infusion pump device. Because fonts are now described in pen strokes (true-type fonts), rather than in pixels (bit-by-bit) this allows the infusion pump device to determine how to display the different fonts. Another option could involve uploading the fonts in strings from various sources, such as the internet.

If so desired, a food library may be downloaded from a PC, or from the internet via a PC. In the food library, each food item will have some information associated with it, for example, carbohydrate count, fat count, proteins, serving size, and the like. The food library may be built directly into the infusion pump device, or it may be downloaded from remote sources, as discussed above. For one example, the food library may be downloaded through a transceiver embodied by the user's cellular telephone. Other options may include eliminating the need to bypass the transceiver every time a food item is selected, such as, downloading the food items from the PC and storing it until use. The food library may also be input directly into the controller device rather than the infusion pump device. If the food library is contained in the infusion pump device, an associated food library menu could be dynamic. The user could select from different layers of the food library the items consumed or about to be consumed and the infusion pump device could calculate the appropriate amount of insulin to be delivered. Variable data could be included for a small food library with less than 50 food items. For example, there could be variable data for a food library dedicated to breakfast foods only. There could be a "breakfast" key or icon on the controller device that the user can select. There may also be "lunch" and "dinner" and "snack" icons.

Communications between the system components may be performed in a variety of manners. In an embodiment using RF options, there could be employed a single frequency or a "spread spectrum" where a large range of RFs can be used to relay the communication. In another embodiment, changing frequencies can be used so as to pick up whatever frequency is present. This is known as "frequency hopping," where the frequency changes every millisecond or so to take advantage of all, or substantially all, frequencies available. In some cases, frequency hopping allows the system to find frequencies that are not being used by other nearby systems and thus avoid interference. In addition, a system may operate in a manner where each component-to-component communication is on a different frequency, or where the delay for each communication is different. Other types of RF, that are not described, may also be used for communication, such as, translation frequency.

According to yet another embodiment of the present invention, an infusion system includes a controller device, with a controller device display, and an infusion device, with an infusion device display, and a method for infusing a fluid into a body of a user is provided. The method includes the steps of: receiving data communication from a user, transmitting with the controller device the communication including data to an infusion device, receiving with the infusion device the communication, and displaying with the controller device display information regarding the fluid delivery, where the display on the controller device display shows information according to instructions or communications sent to the controller device from the infusion device. At any moment, the display of the infusion device may correspond with what is displayed on the infusion device display. The method may further include the step of displaying trends and graphs. Additionally, the method may include the step of inputting an estimate of a material to be ingested by the user, and the estimated amount of fluid to be infused into the body of the user is calculated further based upon the inputted estimate of the material to be ingested by the user.

Although the above description has been focused on use of a controller device with an infusion device, it is appreciated that a controller device as described herein could be used with any number of therapy/diagnostic devices. For example, in any case where a therapy/diagnostic device is tethered to the body, at least partially implanted in the body, or otherwise inconvenient for the user to manipulate while therapy or diagnosis is being performed, a controller device may be used that can send commands to the therapy/diagnosis device and/or mimic the display on the therapy/diagnosis device. Therapies other than infusion of fluids could include electrical therapy, such as electrical therapy for the brain and for conditions such as epilepsy. Diagnostics could include any number of diagnostics, such as information from cardiac and other sensors.

Electrical therapy devices include neurostimulation devices for epilepsy, similar devices for pain management, etc. In addition, there are electro-acupuncture devices, where a needle is inserted into the body much like acupuncture, but additional therapy is delivered by electrical impulses. In certain embodiments, the structure of an electrical therapy device may include a needle that is inserted into appropriate areas of the body. The architecture would be similar to that of the devices described above. The patient/user would use the controller device to deliver "dosages" of electrical impulses to alleviate pain and manage neurological symptoms on demand such as twitching, uncontrolled movement of limbs, spasms, and so forth.

In further embodiments, devices such as those used in physical therapy clinics could be adapted for individual use. For example, a patch or other device placed on the body could be activated by the controller device to deliver said therapy, be it ultrasound, heat or some other media. The architecture for these devices could be similar to the architecture of the devices already described, where a physiological characteristic sensor or infusion device is replaced by a therapy delivering device/mechanism.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are, therefore, to be considered in all respects as illustrative and not restrictive, the scope of the invention being indicated by the appended claims rather than the foregoing description. All changes that come within the meaning of and range of equivalency of the claims are intended to be embraced therein.

What is claimed is:

1. An infusion pump to be carried by a user and controlled by a controller device, the infusion pump being adapted to be attached to the user's body and comprising:
   an infusion pump display;
   a drive mechanism operatively coupled to a reservoir containing a fluid to be infused into the user's body;
   an infusion pump receiver that receives a first communication from the controller device;
   an infusion pump transmitter that transmits a second communication to the controller device;
   a receptacle that receives therein a test strip for testing a first analyte from the user to determine a concentration of the first analyte in the user;
   a processor that processes the determined concentration of the first analyte and the first communication received from the controller device;
   a bolus estimator that calculates, based on the determined concentration of the first analyte and in conjunction with the processor, an estimated amount of said fluid to be infused into the body of the user; and
   an illuminator that is disposed proximate said receptacle and illuminates at least one of the receptacle and the test strip,
   wherein the infusion pump is configured to remain attached to the user's body between successive infusions of said fluid into the user's body, and wherein the controller device includes a controller device display which simultaneously shows substantially the same information as shown on the infusion pump display.

2. The infusion pump of claim 1, wherein the infusion pump display includes a backlight, and wherein the illuminator provides low-intensity illumination when said backlight is on.

3. The infusion pump of claim 2, wherein said low-intensity illumination falls within a range of about 2 to about 5 millicandelas at 110° F.

4. The infusion pump of claim 1, wherein the illuminator provides high-intensity illumination when the test strip is inserted into the receptacle.

5. The infusion pump of claim 4, wherein said high-intensity illumination falls within a range of about 40 to about 50 millicandelas at 110° F.

6. The infusion pump of claim 1, wherein the illuminator is a light-emitting diode (LED).

7. The infusion pump of claim 6, wherein the LED emits white light.

8. The infusion pump of claim 1, wherein the illuminator projects its light up to a distance of about 20 mm.

9. The infusion pump of claim 1, wherein the test strip has an insertion end and a free end, and the illuminator illuminates an area covering at least the test strip's free end when the test strip is inserted into the receptacle.

10. The infusion pump of claim 1, wherein the illuminator activates automatically when the test strip is inserted into the receptacle.

11. The infusion pump of claim 1, wherein the infusion pump further includes an infusion pump housing and wherein each of the drive mechanism, the infusion pump receiver, the infusion pump transmitter, the infusion pump processor, the infusion pump display, the receptacle, and the illuminator is disposed on or in the infusion pump housing.

12. The infusion pump of claim 1, wherein the infusion pump receiver receives data downloaded from a remote station.

13. The infusion pump of claim 12, wherein the remote station is selected from the group consisting of a computer, a hospital database, a cellular telephone, a personal digital assistant, a smart phone, and the Internet.

14. The infusion pump of claim 1, wherein the infusion pump receiver and transmitter are combined into a transceiver.

15. The infusion pump of claim 1, wherein the first communication includes instructions for acts to be performed by the infusion pump and the infusion pump acts in response to the instructions.

16. The infusion pump of claim 1, wherein the infusion pump and the controller device communicate using wireless communication.

17. The infusion pump of claim 16, wherein the wireless communication is one of radio frequency and infrared.

18. The infusion pump of claim 16, wherein the wireless communication is at least one of single frequency communication, spread spectrum communication, and frequency hopping communication.

19. The infusion pump of claim 1, further including a light sensor to measure ambient light, wherein the illuminator activates when a level of ambient light measured by the light sensor falls below a pre-determined level.

20. The infusion pump of claim 1, wherein the first analyte is blood glucose.

21. The infusion pump of claim 1, wherein said fluid is insulin.

* * * * *